United States Patent
Schwartz et al.

(10) Patent No.: US 10,493,123 B2
(45) Date of Patent: Dec. 3, 2019

(54) METHOD OF TREATING OVERWEIGHT OR OBESITY COMPRISING ADMINISTERING A PLEUROTUS OSTREATUS MUSHROOM EXTRACT OR A COMPOSITION COMPRISING A PLEUROTUS OSTRETUS MUSHROOM EXTRACT

(71) Applicant: Yissum Research Development Company of The Hebrew University of Jerusalem LTD., Jerusalem (IL)

(72) Inventors: Betty Schwartz, Rehovot (IL); Einav Yehuda-Shnaidman, Modiin (IL); Lili Nimri, Nazareth (IL)

(73) Assignee: YISSUM RESEARCH DEVELOPMENT COMPANY OF of The Hebrew University of Jerusalem LTD., Jerusalem (IL)

( * ) Notice: Subject to any disclaimer, the term of this patent is extended or adjusted under 35 U.S.C. 154(b) by 0 days.

(21) Appl. No.: 15/127,022

(22) PCT Filed: Mar. 18, 2015

(86) PCT No.: PCT/IL2015/050283
§ 371 (c)(1),
(2) Date: Sep. 18, 2016

(87) PCT Pub. No.: WO2015/140798
PCT Pub. Date: Sep. 24, 2015

(65) Prior Publication Data
US 2017/0368133 A1 Dec. 28, 2017

Related U.S. Application Data

(60) Provisional application No. 61/955,338, filed on Mar. 19, 2014, provisional application No. 62/082,308, filed on Nov. 20, 2014, provisional application No. 61/955,874, filed on Mar. 20, 2014.

(51) Int. Cl.
*A61K 38/57* (2006.01)
*A61K 38/04* (2006.01)

(52) U.S. Cl.
CPC ............ *A61K 38/04* (2013.01); *A61K 38/57* (2013.01); *Y02A 50/473* (2018.01)

(58) Field of Classification Search
None
See application file for complete search history.

(56) References Cited

U.S. PATENT DOCUMENTS

| | | | | |
|---|---|---|---|---|
| 2002/0164352 A1* | 11/2002 | Donatini | ............ | A61K 31/722 424/195.15 |
| 2003/0161842 A1* | 8/2003 | Wang | ............ | A61K 36/07 424/195.15 |
| 2004/0137602 A1* | 7/2004 | Kitajima | ............ | A01G 18/00 435/254.1 |
| 2010/0249248 A1* | 9/2010 | Ogura | ............ | A61K 36/00 514/724 |

FOREIGN PATENT DOCUMENTS

| | | | |
|---|---|---|---|
| JP | 07/238091 | * | 9/1995 |
| JP | 7-238091 | * | 9/1995 |
| JP | 1995238091 | | 9/1995 |
| JP | H7-238091 | | 9/1995 |
| WO | WO 2004 096252 | * | 11/2004 |
| WO | WO 2012 165735 | * | 12/2012 |

OTHER PUBLICATIONS

Nimri L. et al. Ostreolysin Induces Browning of Adipocytes and Ameliorates Hepatic Steatosis. Gastroenterology and Hepatology 33 (4)1-11, Apr. 16, 2018. (Year: 2018).*
Lee J. et al. Extraction and Characteristics of Anti-Obesity Lipase Inhibitor From Phellinus lineus. Mycobiology 38(1)52-57, 2010. (Year: 2010).*
Kanagasabapathy G. et al. Beta-Glucan Rich Extract from Pleurotus sajor-caju . . . Evidence Based Complementary and Alternative Medicine vol. 2013, pp. 1-10, May 7, 2013. (Year: 2013).*
Berne S. et al. Effect of pH on the Pore Forming Activity and Conformational Stability of Ostreolysin . . . Biochemistry 44:11137-47, 2005. (Year: 2005).*
Corrado et al. Review of Treatment options for Nonalcoholic Fatty Liver Disease.
European Search Report for EP Application No. EP 17 18 2284 dated Jan. 31, 2018.
Ravussin, E. J.E. Galgani, "The implication of brown adipose tissue for humans". Annu Rev Nutr, 2011. 31: p. 33-47.
Berne, S., et al., "Pleurotus and Agrocybe hemolysins, new proteins hypothetically involved in fungal fruiting". Biochim Biophys Acta. 2002. 1570(3): p. 153-9.
Sepcic, K., et al., "Interaction of ostreolysin, a cytolytic protein from the edible mushroom Pleurotus ostreatus, with lipid membranes and modulation by lysophospholipids". Eur J Biochem, 2003. 270(6): p. 1199-210.
Zuzek, M.G., et al., "Toxic and lethal effects of ostreolysin, a cytolytic protein from edible oyster mushroom (*Pleurotus ostreatus*), in rodents". Toxicon. 2006. 48(3): p. 264-71.
Patra, S.K.. "Dissecting lipid raft facilitated cell signaling pathways in cancer". Biochim Biophys Acta, 2008. 1785(2): p. 182-206.

(Continued)

*Primary Examiner* — Ralph J Gitomer
(74) *Attorney, Agent, or Firm* — The Roy Gross Law Firm, LLC; Roy Gross

(57) ABSTRACT

Disclosed are methods for treating, preventing and alleviating obesity, fatty liver syndrome, diabetes, one or more metabolic syndrome conditions or complications and/or cancer comprising administering an effective amount of ostreolysin, its functionally related variant, or an extract or mushroom extract comprising the same to subjects in need thereof.

11 Claims, 21 Drawing Sheets

Specification includes a Sequence Listing.

(56) References Cited

OTHER PUBLICATIONS

Fan, J.Y., et al., "Morphological changes of the 3T3-L1 fibroblast plasma membrane upon differentiation to the adipocyte" form. J Cell Sci, 1983. 61: p. 219-30.

Kumar, N., et al., Orphan nuclear receptor NOR-1 enhances 3',5'-cyclic adenosine 5'-monophosphate-dependent uncoupling protein-1 gene transcription. Mol Endocrinol, 2008. 22(5): p. 10574.

Elabd, C., et al., "Human multipotent adipose-derived stem cells differentiate into functional brown adipocytes". Stem Cells, 2009. 27(11): p. 2753-60.

Yehuda-Shnaidman, E., et al., "Acute stimulation of white adipocyte respiration by PKA-induced lipolysis. Diabetes", 2010. 59(10): p. 2474-83.

De Leeuw, M., et al., "Binding assay and preliminary X-ray crystallographic analysis of ACTIBIND, a protein with anticarcinogenic and antiangiogenic activities". Acta Crystallogr Sect F Struct Biol Cryst Commun, 2007. 63(Pt 8): p. 716-9.

Tseng, Y.H., et al., "New role of bone morphogenetic protein 7 in brown adipogenesis and energy expenditure". Nature, 2008. 454(7207) p. 1000-4.

Le Lay, S., et al., "Filling up adipocytes with lipids". Lessons from caveolin-1 deficiency. Biochim Biophys Acta, 2009. 1791(6): p. 514-8.

Couet, J., et al., "Identification of peptide and protein ligands for the caveolin-scaffolding domain". Implications for the interaction of caveolin with caveolae-associated proteins. J Biol Chem, 1997. 272(10): p. 6525-33.

Cinti S. "The role of brown adipose tissue in human obesity". Nutrition, Metabolism & Cardiovascular Diseases, 2006. 16, p. 569-74.

Tiraby C et al. "Acquirement of brown fat cell features by human white adipocytes". J Biol Chem, 2003. 278(35): p. 33370-6.

Berlanga, A et al. "Molecular pathways in non-alcoholic fatty liver disease". Clin Exp Gastroenterol (2014). 7, pp. 221-239.

Dietrich, P. et al. "Non-alcoholic fatty liver disease, obesity and the metabolic syndrome". Best Pract Res Clin Gastroenterol (2014). 28, pp. 637-653.

Dyson, J.K. et al. "Non-alcoholic fatty liver disease: a practical approach to treatment". (2014). Frontline Gastroenterol 5, pp. 277-286.

Gruben, N et al. "Nonalcoholic fatty liver disease: A main driver of insulin resistance or a dangerous liaison?" Biochim Biophys Acta (2014). 1842, pp. 2329-2343.

Booth et al., Immunol. Lett. 19:65-70 (1988).

Gardella et al., J. Biol. Chem. 265:15854-15859 (1990).

Choi et al., "Protease-Activated Drug Development", Theranostics, vol. 2(2), pp. 156-178 (found in http://www.thno.org/v02p0156.pdf).

Tal, Dana M.Sc. et al.: "A recombinant fungal compound Ostreolysin, induces anti-profiferative and proapoptoticeffects on colon cancer cells" Conference Proceeding. II Anticancer Drugs Meeting Aug. 22, 2013. Stockholm, Sweeden Retrieved from the Internet: URL:http://www.scopemed.org/?jft=100&ft=10 [retrieved on Sep. 3, 2015] the whole document.

V K Singh et al: "Corresponding Author: Medicinal Properties of pleurotus Species (Oyster Mushroom): A Review" World Journal of Fungal and Plant Biology, Jan. 1, 2012, pp. 1-12, XP055206985.

Wasonga Cg et al.: "Mushroom polysaccharide extracts delay progression of carcinogenesis in mice" Journal of Experimental Therapeutics and Oncology, Rapid Science Publishers, London, GB. vol. 7 No. 2, Jan. 1, 2008, pp. 147-152.

Nuhu Alam et al.: "Hypolipidemic Activities of Dietary Pleurotus ostreatus in Hypercholesterolemic Rats" Mycobiology vol. 39. No. 1, Jan. 1, 2011 p. 45.

Sachin L. Badole et al.: "Interaction of Aqueous Extract of Pleurotus pulmonaries (Fr.) Quel-Champ". With Glyburide in Alloxan Induced Diabetic Mice Evidence-Based Complementary and Alternative Medicine vol. 5. No. 2, Jun. 1, 2008 pp. 159-164.

Rop O et al.: "Beta-glucans in higher fungi and their health effects" Nutrition Reviews, Allen press, Lawrence, KS, US vol. 67 No. 11, Nov. 1, 2009 pp. 624-631.

Anonymous: "Fungiology, Organic Plerotus ostreatus (Oyster Mushroom), 3.52 oz (100g) Poder Fungiology, Organic Pleurotus ostreatus (Oyster Mushroom)" Sep. 20, 2013. Retrieved from the Internet: URL: https://web.archive.org/web/20130920204616/http://www.iherb.com/Fungiology-Organic-Pleurotus-Ostreatus-Oyster-Mushroom-3-5-2oz-100g-Powder/50610 [retrieved on Aug. 10, 2015].

Gunde-cimerman N et al."Pleurotus Fruiting Bodies contain the inhibitor of 3-hydroxy-3-methylglutaryl-coenzyme a reductase-lovastatin" experimental mycology, academic press london, gb, vol. 19. Jan. 1, 1995 pp. 1-06.

Iris Lavi et al.: " Glucans from the edible mushroominhibit, colitis-associated colon carcinogenesis in mice" Journal of Gastroenterology, Springer-Verlag, TO, vol. 47, No. 5, Dec. 21, 2011, pp. 504-518.

Susan Z. Yanovski et al.: "Long-term Drug Treatment for obesity" JAMA vol. 311, No. 1 Jan. 1, 2014, p. 74.

International Search Report for PCT Application No. PCT/IL2015/050283 dated Dec. 16, 2015.

Jemal A, et al. Cancer statistics, 2010. CA Cancer J Clin 2010;60:277-300.

The Israeli National Cancer Registry. [updated 2007]. Available from: http://www.health.gov.il/Download/pages/mabatB_191109.pdf (Nov. 2011).

Innos K, et al. "Survival for colon and rectal cancer in Estonia: Role of staging and treatment". Acta Oncol. Nov. 18, 2011 18. [Epub ahead of print] PubMed PMID: 22098601.

Sloan EK et al. "Caveolin-1 inhibits breast cancer growth and metastasis". Oncogene 2004;23:7893-7.

Lazebnik YA et al. "Cleavage of poly (ADP-ribose) polymerase by a proteinase with properties like ICE". Nature. Sep. 22, 1994;371(6495):346-7.

Oliver FJ et al. "Importance of poly(ADP-ribose) polymerase and its cleavage in apoptosis". Lesson from an uncleavable mutant. J Biol Chem. Dec. 11, 1998;273(50):33533-9.

Lalier L et al. "Bax activation and mitochondrial insertion during apoptosis. Apoptosis". May 2007;12(5):887-96.

Malicev E et al. "Effect of ostreolysin, an Asp-hemolysin isoform, on human chondrocytes and osteoblasts, and possible role of Asp-hemolysin in pathogenesis". Med Mycol. Mar. 2007;45(2):123-30.

Chowdhury HH et al. "Lysophospholipids prevent binding of a cytolytic protein ostreolysin to cholesterol-enriched membrane domains". Toxicon. Jun. 15, 2008:51(8):1345-56.

Parton RG et al. "The multiple faces of caveolae". Nat Rev Mol Cell Biol. Mar. 2007;8(3):185-94.

Patel, Yashvant, Ram Naraian, and V. K. Singh. "Medicinal properties of pleurotus species (oyster mushroom): a review." World Journal of Fungal and Plant Biology 3.1 (2012): 1-12.

Wasonga, C. G., Okoth, S. A., Mukuria, J. C., & Omwandho, C. O. (2008). Mushroom polysaccharide extracts delay progression of carcinogenesis in mice. Journal of experimental therapeutics & oncology, 7(2), 147-152.

Alam, Nuhu, Ki Nam Yoon, and Tae Soo Lee. "Antihyperlipidemic activities of Pleurotus ferulae on biochemical and histological function in hypercholesterolemic rats," Journal of research in medical sciences: the official journal of Isfahan University of Medical Sciences 16.6 (2011): 776.

Fungiology, 3.52 oz powder Organic Pleurotus ostreatus (Oyster Mushroom), www.iherb.com.

Office Action for IL Application No. 247838 dated Nov. 22, 2018.

Office Action for JP application No. 2017-500471 dated Nov. 6, 2018.

* cited by examiner

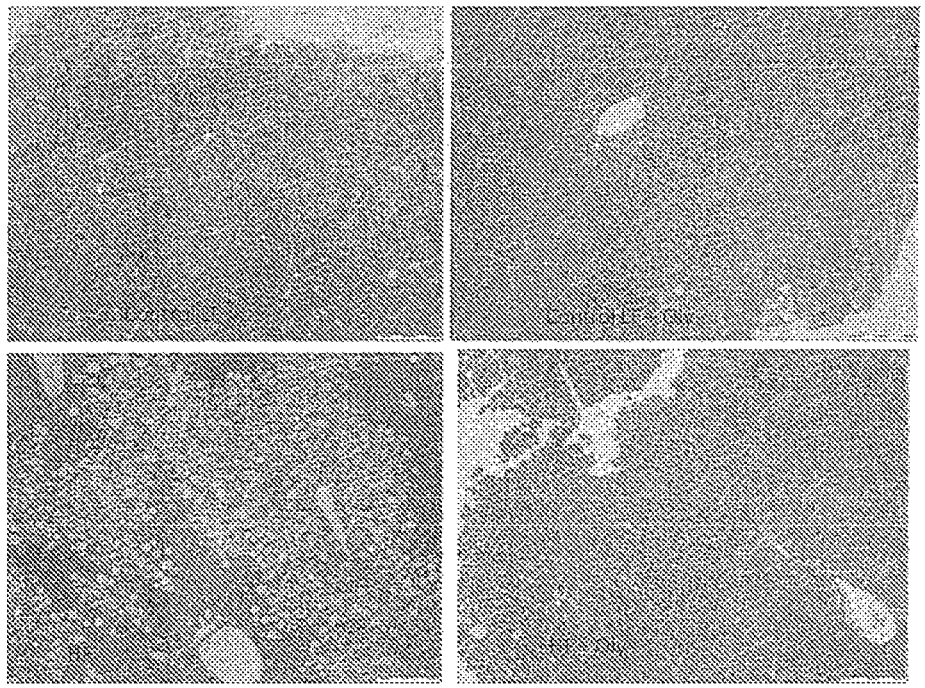
FIGURE 19A  FIGURE 19B
FIGURE 19C  FIGURE 19D
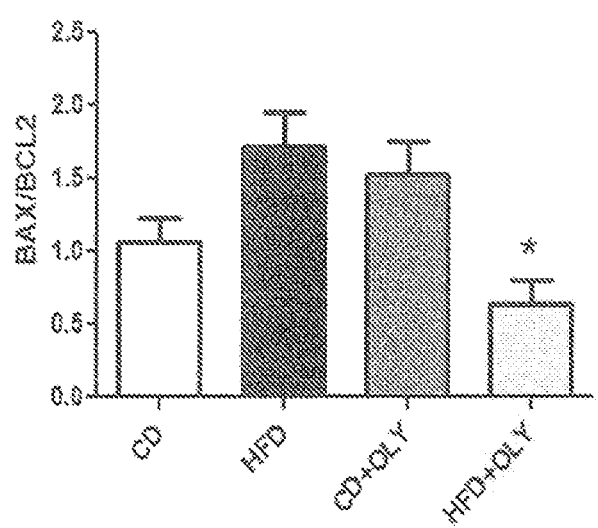
FIGURE 20

FIGURE 21A
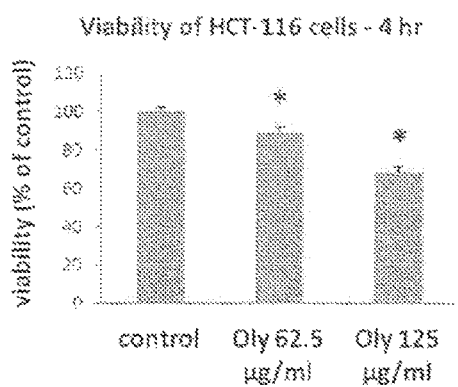
FIGURE 21B
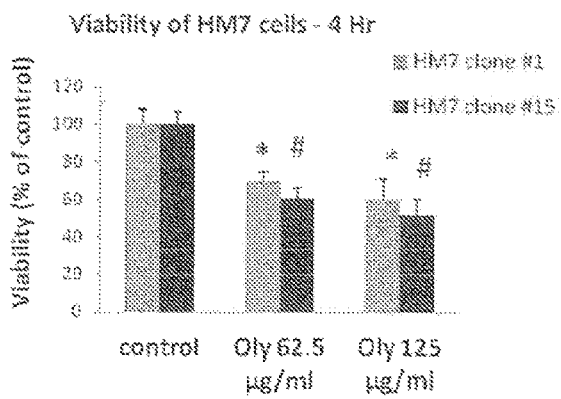
FIGURE 21C
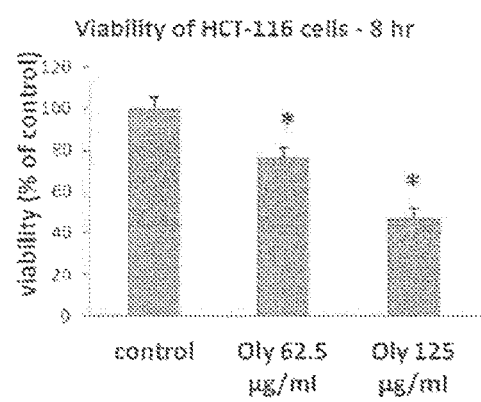
FIGURE 21D
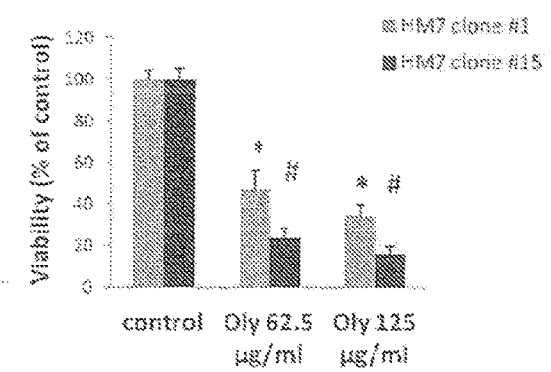
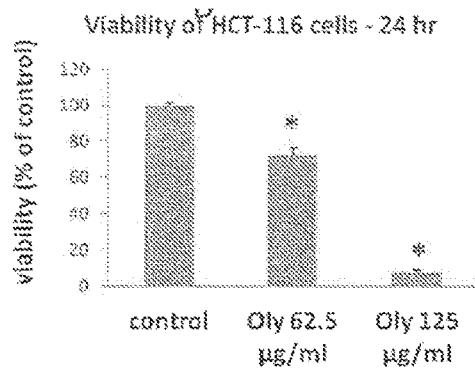
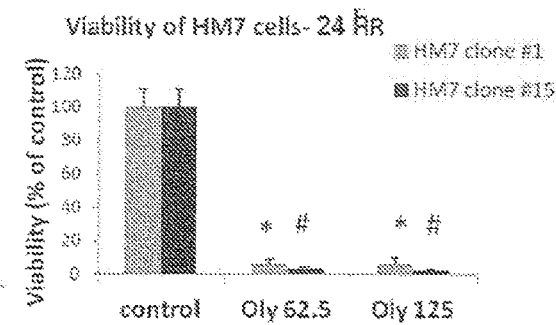
FIGURE 21E
FIGURE 21F

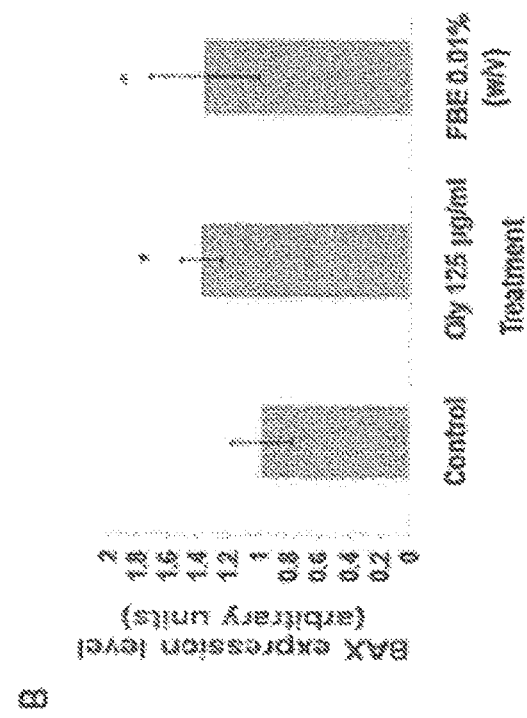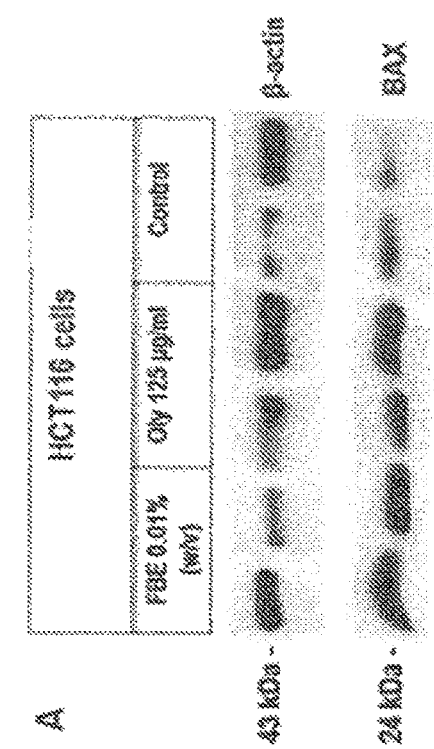

SEQUENCE LISTING

<160> NUMBER OF SEQ ID NOS: 1

<210> SEQ ID NO 1
<211> LENGTH: 137
<212> TYPE: PRT
<213> ORGANISM: Pleurotus aff. ostreatus

<400> SEQUENCE: 1

```
Ala Tyr Ala Gln Trp Val Ile Ile Ile Ile His Asn Val Gly Ser Gln
1               5                   10                  15

Asp Val Lys Ile Lys Asn Leu Lys Ala Ser Trp Gly Lys Leu His Ala
            20                  25                  30

Asp Gly Asp Lys Asp Ala Glu Val Ser Ala Ser Asn Tyr Glu Gly Lys
        35                  40                  45

Ile Ile Lys Pro Asp Glu Lys Leu Gln Ile Asn Ala Cys Gly Arg Ser
    50                  55                  60

Asp Ala Ala Glu Gly Thr Thr Gly Thr Phe Asp Leu Val Asp Pro Ala
65                  70                  75                  80

Asp Gly Asp Lys Gln Val Arg His Phe Tyr Trp Asp Cys Pro Trp Gly
            85                  90                  95

Ser Lys Thr Asn Thr Trp Thr Val Ser Gly Ser Asn Thr Lys Trp Met
            100                 105                 110

Ile Glu Tyr Ser Gly Gln Asn Leu Asp Ser Gly Ala Leu Gly Thr Ile
        115                 120                 125

Thr Val Asp Thr Leu Lys Lys Gly Asn
130                 135
```

METHOD OF TREATING OVERWEIGHT OR OBESITY COMPRISING ADMINISTERING A PLEUROTUS OSTREATUS MUSHROOM EXTRACT OR A COMPOSITION COMPRISING A PLEUROTUS OSTRETUS MUSHROOM EXTRACT

CROSS-REFERENCE TO RELATED APPLICATIONS

This application is a National Phase Application of PCT International Application No. PCT/IL2015/050283, International Filing Date Mar. 18, 2015, claiming the benefit of U.S. Provisional Patent Applications Nos. 61/955,338, filed Mar. 19, 2014, 62/082,308, filed Nov. 20, 2014 and 61/955,874, filed Mar. 20, 2014, all of which are hereby incorporated by reference.

FIELD OF INVENTION

The invention is directed to the use of ostreolysin (oly), functionally related variant thereof, or extract or mushroom extract comprising oly for treating, preventing, alleviating and/or reducing one or more condition or complication associated with metabolic syndrome or for treating or preventing obesity, fatty liver, diabetes and/or cancer.

BACKGROUND OF THE INVENTION

Obesity is at epidemic proportions with more than 300 million obese people world-wide and constantly rising. Obesity is not only a cosmetic problem, but a life-threatening disease, reducing quality of life as well as its longevity. Obesity increases the risk for many dreadful diseases, including type 2 diabetes, cardiovascular diseases and cancer, and is associated with insulin resistance, glucose intolerance and dyslipidemia. Therefore, there is an important need to understand the mechanisms related to obesity and find ways to combat the deadly disease and its complications.

As a treatment perspective, finding an appropriate cure for obesity and related complications is extremely challenging due to the physiological and biochemical complexity of the disease. However, it is clear that changing energy homeostasis in favor of energy expenditure vs. energy intake will help in combating obesity. Therefore, identification of cellular mechanisms able to increase whole body energy expenditure ("negative energy balance") are advantageous as targets for obesity therapy.

One option to increase energy expenditure is the uncoupling of mitochondrial respiration in brown adipose tissue (BAT). In this process, there is a regulated proton leak in the inner mitochondrial membrane through uncoupling protein 1 (UCP1), resulting in the dissipation of energy as heat and increased fuel oxidation. This suggests that high amounts of active BAT would be beneficial in the battle against obesity. Unfortunately, however, human adults are not considered to have sufficient amounts of BAT, in contrast to small mammals and newborn humans. Therefore, finding ways to increase the activity of BAT in adulthood would be beneficial in combating obesity by increasing the oxidation of nutrients in the body.

The recent discovery of BAT in human adults and a better understanding of BAT development have encouraged the quest for new alternatives to treat obesity since obese individuals seem to have less brown adipose tissue mass/activity than do their lean counterparts. It is noteworthy that the activity of BAT is approximately fourfold higher in the lean group than in the overweight/obese group.

From an anatomical point of view, brown fat cells are localized in two types of depots: discrete and diffuse. In humans, BAT of discrete location is found in cervical-supraclavicular, perirenal/adrenal, and paravertebral regions around the major vessels and is probably present to generate and distribute heat to maintain core temperature. In distinction, diffuse brown fat cells exist in white adipose and appear in response to cold exposure or chronic catecholamine stimulation.

The metabolic syndrome, which comprises a cluster of metabolic abnormalities such as hyperlipidaemia, diabetes mellitus and hypertension, is a widespread and increasingly prevalent disease in western and industrialized countries.

Non-alcoholic fatty liver disease (NAFLD) is now recognized as the hepatic manifestation of the metabolic syndrome and is emerging as one of the most common causes of chronic liver disease worldwide. NAFLD encompasses a wide disease spectrum ranging from simple hepatic steatosis to steatohepatitis, advanced fibrosis and cirrhosis. Liver-related morbidity and mortality due to NAFLD are observed in patients who have advanced fibrosis and cirrhosis. The mechanisms that accelerate the progression of simple steatosis towards more debilitating and advanced stages of NAFLD remain poorly understood, but generally assume that it implies a two hit theory. Hepatic fat accumulation represents the 'first hit' of the disease and it has been suggested that fat accumulation in hepatocytes is the hallmark of NAFLD and leaves them highly vulnerable to a 'second hit', for example, injury by oxidative stress and inflammatory cytokines, such as TNF-α, monocyte chemoattractant protein-1 (MCP-1) and other cytokines.

At present, no pharmacotherapy is available that can fully reverse or prevent steatohepatitis. Therefore, it is necessary to develop effective therapies for the treatment of NAFLD and the discovery of molecules or compositions that may reduce the risk of NAFLD would be useful.

Colorectal cancer (CRC) is the second leading cause of death from cancer among adults in the United States as well as in Israel. Mortality rates are in constant rise, which is why there is so much importance in finding factors that would reduce morbidity. As a treatment perspective, finding an appropriate cure for cancer and related complications is extremely challenging due to the complexity of the mechanisms involved in this disease progression. Therefore, identification of cellular mechanisms involved and molecules able to suppress colon cancer cell proliferation and progression could be advantageous for cancer treatment.

Caveolin-1 (Cav-1) is the major protein component of caveolae, specialized lipid rafts that are recognized in electron micrographs as 50-100 nm invaginations of the plasma membrane. Caveolae are found primarily in terminally differentiated mesenchymal cells including adipocytes, endothelial cells and fibroblasts suggesting a possible role of Cav-1 as a negative regulator of cell proliferation. Interestingly, Cav-1 has been implicated in the pathogenesis of oncogenic cell transformation, tumorigenesis and metastasis. Cells, including tumor cells, constantly face the decision of whether to survive and proliferate or to undergo programmed cell death (apoptosis). Therefore, identifying the pathways that are pro-apoptotic or anti-apoptotic has important implications for controlling tumor cell growth.

SUMMARY OF THE INVENTION

In some embodiments of the invention, there is provided a method for treating, preventing or reducing the severity of one or more conditions or complications associated with metabolic syndrome in a subject in need, comprising: administering a composition comprising an effective amount of oly, oly functionally related variant or a combination thereof to the subject in need.

According to some embodiments of the invention, the one or more conditions or complications associated with metabolic syndrome is overweight, obesity, lipodystrophy, fatty liver, NAFLD, NASH, chronic liver disease, cirrhosis or hepatocellular carcinoma.

According to some embodiments of the invention, the one or more conditions or complications associated with metabolic syndrome is high blood/plasma glucose levels, glucose intolerance type II diabetes, high cholesterol levels, high lipid levels, or high triglyceride levels.

According to some embodiments of the invention, there is provided a method for treating, preventing, decreasing or reducing cancer in a subject in need comprising administering a composition comprising an effective amount of oly, oly functionally related variant or a combination thereof to the subject in need thereof.

According to some embodiments of the invention, the cancer is colon cancer.

According to some embodiments of the invention, the oly is a recombinant protein.

According to some embodiments of the invention, the oly is produced in a prokaryotic cell.

According to some embodiments of the invention the prokaryotic cell is a bacterial cell.

According to some embodiments of the invention there is provided a formulation comprising an effective amount of oly, oly functionally related variant or a combination thereof for treating, preventing, decreasing or reducing cancer.

According to some embodiments of the invention, the cancer is a colon cancer.

According to some embodiments of the invention, there is provided a formulation comprising oly, oly functionally related variant or combination thereof, for treating, preventing or reducing the severity of one or more conditions or complications associated with metabolic syndrome.

According to some embodiments of the invention, the one or more conditions or complications associated with metabolic syndrome is overweight, obesity, fatty liver, NAFLD, NASH, chronic liver disease, cirrhosis or hepatocellular carcinoma.

According to some embodiments of the invention, the one or more conditions or complication is associated with metabolic syndrome is high blood/plasma glucose levels, glucose intolerance type II diabetes, high cholesterol levels, high lipid levels, or high triglyceride levels.

According to some embodiments of the invention, the formulation is a pharmaceutical formulation.

According to some embodiments of the invention, treating obesity or overweight is associated with differentiating white adipocyte into brown adipocyte in a cell or inducing brown adipogenesis in a cell.

According to some embodiments of the invention, the gene expression of brown adipogenesis markers is increased following the treatments described herein.

According to some embodiments of the invention there is provided a method for treating, preventing or reducing the severity of at least one or more conditions or complications associated with metabolic syndrome in a subject in need comprising administering an effective amount of an extract comprising oly or mushroom extract comprising oly, or a composition comprising an extract comprising oly or mushroom extract comprising oly to the subject in need.

According to some embodiments of the invention, the one or more condition or complication associated with metabolic syndrome is overweight, obesity, lipodystrophy, fatty liver, NAFLD, NASH, chronic liver disease, cirrhosis or hepatocellular carcinoma.

According to some embodiments of the invention, the one or more condition or complication associated with metabolic syndrome is high blood/plasma glucose levels, glucose intolerance type II diabetes, high cholesterol levels, high lipid levels, or high triglyceride levels.

According to some embodiments of the invention there is provided a method for treating, preventing, decreasing or reducing cancer in a subject in need comprising administering an effective amount of an extract comprising oly or mushroom extract comprising oly or a composition comprising an extract comprising oly or mushroom extract comprising oly to the subject in need.

According to some embodiments of the invention, the cancer is colon cancer.

According to some embodiments of the invention there is provided an extract or mushroom extract comprising oly or a formulation comprising an effective amount of an extract or mushroom extract comprising oly, for treating, preventing or reducing the severity of one or more condition or complication associated with metabolic syndrome.

According to some embodiments of the invention there is provided an extract or mushroom extract comprising oly or a formulation comprising an effective amount of an effective amount of an extract or mushroom extract comprising oly for treating, preventing, decreasing or reducing cancer.

According to some embodiments of the invention, the formulation is a nutraceutical formulation, a food additive or a food supplement.

According to some embodiments of the invention, the mushroom extract is derived from *Pleurotus* mushroom.

According to some embodiments of the invention, the *Pleurotus* mushroom is *Pleurotus ostreatus* mushroom or *Pleurotus pulmonarious* mushroom.

According to some embodiments of the invention, the extract or the formulation described herein are in a form of a powder, solution, enteric coated table, suspension, emulsion, tablet, or capsule, an enteric coated tablet, gel, cream, ointment, foam, paste or injection.

According to some embodiments of the invention, the formulation is a nutraceutical composition or a dietary supplement and comprises a carrier suitable for food consumption.

BRIEF DESCRIPTION OF THE FIGURES

FIG. 5B provides representative confocal microscopic images of HIB-1B and 3T3-L1 cells, treated (oly-10 μg/ml, 48 hours) or not (control) and stained with Nile red, a lipid detector dye.

FIG. 19 A-D are images presenting the histological results of livers of the mice on the day of sacrifice; Control LF (19A), Control LF+oly (19B), HF (19C) and HF+oly (19D).

FIG. 20 is a graph representing the apoptosis assessment (BAX/BCL2) in the livers of the mice on day of sacrifice (P<0.05).

FIGS. 21A-F show the cytotoxic activity of Ostreolysin (oly) towards HCT116 cells (21A, C and E) and HM7 clone #1 and clone #15 cells (21B, D and F). Cells were grown overnight in Dulbecco's modified Eagle's medium and treated with various concentrations of Ostreolysin, as indicated in the Examples Section for 4 (21A and B), 8 (21C and D), 24 (21E and F) hours. Cell viability was estimated by the MTT assay. Viability (%) was expressed as the ratio between formazan absorbance at 550 nm of treated cells at different time intervals and control cells at the beginning of the experiment. Each point represents the mean±SE from four independent experiments performed in n=4 replicates. Error bars are not distinguishable since they are smaller than symbol size.

FIG. 22A presents cells treated with Oly 125 μg/ml or FBE 0.01% (w/v), or left untreated as control for 8 hours. Following incubation cells were harvested, permeabilized, stained with Propidium Iodide and analyzed. Results are representative of one out of two independent experiments each performed in triplicates. Data were obtained from 15,000 HCT116 cells. As presented in FIG. 22B, the cell cycle was analyzed using WinMDI 2.9 software of HCT116 cell line treated with Oly 125 μg/ml, FBE 0.01% (w/v) or left untreated as control and finally permeabilization and staining as described above. All cell phases are represented as percentage. Data shown are the mean±SE of two independent experiments, each performed in triplicates. Data were obtained from 15,000 HCT116 cells.

FIGS. 23 A-C depict the effect of recombinant Oly on cleavage of PARP-1 and BAX expression level in HCT116 cells. Cells were incubated for 8 hours in the presence or absence of Oly or FBE (Fruiting Bodies Extract). Total cell lysates (for PARP-1 and BAX proteins) were processed for western blot analysis as described in methods. FIG. 23B: Data shown are representative of one out of four independent experiments, each performed in duplicates. Equal loading was confirmed by probing each blot for (β-actin. FIG. 23C: Quantification by densitometric analysis was performed using Gelpro32 analyzer software. Results are expressed as mean±SE (n=4) and statistical analysis indicated higher expression of BAX in HCT116 cells treated with Oly versus untreated cells at P-value<0.05 (student's t-test).

DETAILED DESCRIPTION OF THE INVENTION

Figure 1:
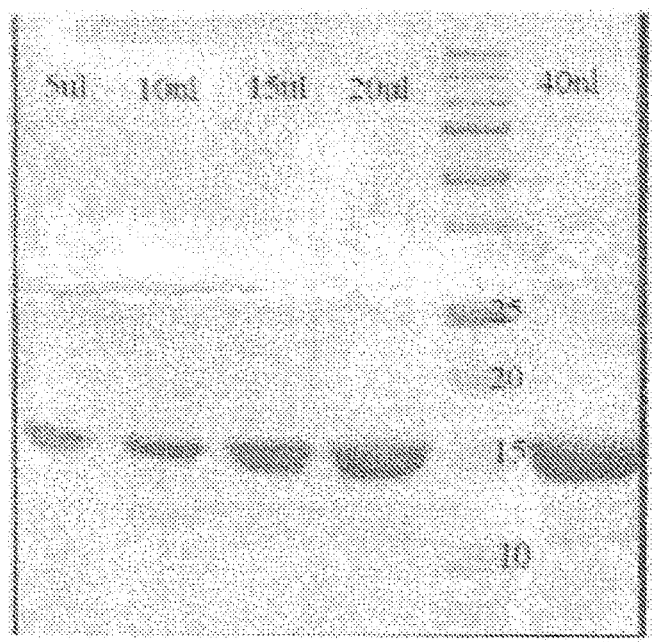
FIG. 1 presents an SDS-PAGE image. Lyophilized oly purity was determined by SDS-PAGE (15%) in the presence of a reducing agent. The respective 40 to 5 µl correspond to 10, 5, 3.75, 2.5 and 1.25 µg/lane.

Embodiments of the invention are directed to a method for preventing, alleviating and/or reducing one or more condition or complication associated with metabolic syndrome or for treating or preventing obesity, lipodystrophy, fatty liver, diabetes and/or cancer, the method comprising administering to a subject a therapeutically effective amount of oly, oly functionally related variant, or a composition comprising oly or oly functionally related variant. In some embodiments, the subject is administered with an extract or mushroom extract comprising oly or a composition comprising an extract or mushroom extract comprising oly. In some embodiments of the invention, the mushroom extract is an extract from *Pleurotus* mushroom. In some embodiments of the invention, the *Pleurotus* mushroom is derived from *Pleurotus ostreatus* mushroom. In some embodiments of the invention, the *Pleurotus* mushroom is derived from *Pleurotus pulmonarious* mushroom. It is noted that throughout the application, unless specifically mentioned otherwise, the term "treating" is meant to include "preventing", "reducing the effects/severity of the condition" "slowing down the progression of the condition", "reducing/eliminating at least one undesired side effect of the condition" and the like. The term "preventing" means that the compounds of the present invention are useful when administered to a patient who has not been diagnosed as possibly having the disease at the time of administration, but who may be expected to develop the disease or be at increased risk for the disease. The oly or its functionally related variant or an extract comprising oly or a composition comprising oly or its functionally related variant or an extract comprising oly of the invention will slow the development of disease symptoms, delay the onset of the disease, or prevent the individual from developing the disease at all. Preventing also includes administration of the compounds of the invention to those individuals thought to be predisposed to the disease due to age, familial history, genetic or chromosomal abnormalities, and/or due to the presence of one or more biological markers for the disease, such as a known genetic mutation.

The use of oly or its functionally related variant or an extract comprising oly can prevent, retard, or improve various metabolic diseases or disorders (e.g., obesity, metabolic syndrome, insulin resistance, diabetes, (including type 2 diabetes), and dyslipidemia) and their clinical complications such as acute myocardial infarction ("heart attack") and aortic stenosis and other cardiovascular complications such as but not limited to atherosclerosis; chronic kidney disease (particularly in view of diabetes impact on kidney vasculature); arterial calcification; valvular calcification, including but not limited to aortic or mitral calcification; valvular stenosis, including but not limited to, aortic or mitral valve stenosis; acute myocardial infarction; restenosis after coronary intervention; accelerated tissue damage or delayed healing after coronary intervention, including but not limited to: valve implantation (including bioprosthetic valve implantation); stent implantation; implantation of engineered tissues, allograft, homograft (including but not limited to, Ross procedure), bioprosthesis tissues, Dacron grafts or any synthetic or bioprosthetic conduit; heart transplantation; arterial or vein graft implantation (including but not limited to, saphenous vein bypass grafts and hemodialysis AV shunts); stroke; and heart failure; failure of vein grafts for coronary bypass surgery; diabetic nephropathy; vasculitis; retinopathy; erectile dysfunction; and non-cardiovascular complications such as, but not limited to, pancreatitis; nonalcoholic fatty liver disease; neuroinflammation; cognitive impairment; cancer. In treating or preventing the diseases or conditions mentioned in the application, the compounds or extracts of the invention are administered in a therapeutically effective amount. The therapeutically effective amount will vary depending on the particular compound used and the route of administration, as is known to those skilled in the art.

Further, the amount of a composition to be administered will, of course, depend on the subject being treated, the severity of the affliction, the manner of administration, the judgment of the prescribing physician, and all other relevant factors. Determination of the exact dose to be administered is conducted by methods known to a person of skill in the art.

In some embodiments of the invention, the amount of oly or the functional variant thereof in a single treatment is calculated to be between about 0.10-10 mg/kg body weight (BW) per day. In some embodiments of the invention, an amount of oly between about 0.3-1.0 mg/kg is used per day. In some embodiments, an amount of between about 0.5-0.8 mg/kg is used per day.

In case of an extract or a mushroom extract that comprises oly, the amount of the dry extract to be administered may be calculated according to the amount of the oly therein. In some embodiments, between about 20-200 mg freeze dried powdered *Pleurotus* or *Pleurotus ostreatus*/Kg body weight (BW) is used per day. In some embodiments, between about 20-60 mg freeze dried powdered *Pleurotus ostreatus*/Kg BW is used per day. In some embodiments, between about 40-50 mg freeze dried powdered *Pleurotus ostreatus*/Kg BW is used per day.

Typically it is contemplated that treatment with oly, its fuctionally related variant or extract comprising oly or a mushroom extract comprising oly would be given at least once per day, typically once, twice, three times or four times per day with the doses given at equal intervals throughout the day and night in order to maintain a constant presence of the drug in order to induce sufficient effect. However, the skilled artisan will be aware that a treatment schedule can be optimized for any given patient, and that administration of compound may occur less frequently than once per day.

The treatment may be carried out for as long a period as necessary. Typically it is contemplated that treatment would be continued indefinitely while the disease state persists, although discontinuation might be indicated if the compounds no longer produce a beneficial effect. The treating physician will know how to increase, decrease, or interrupt treatment based on patient response.

In some embodiments of the invention, the extract or the mushroom extract comprises oly in a concentration of at least 0.001 mg/g extract powder. In some embodiments of the invention, the extract or the mushroom extract comprises oly in a concentration of at least 0.005 mg/g powder. In some embodiments of the invention, the extract or the mushroom extract comprises oly in a concentration of at least 0.01 mg/g powder. In some embodiments of the invention, the extract or the mushroom extract comprises oly in a concentration of at least 0.02, 0.03, 0.04, 0.05, 0.06, 0.07, 0.08, 0.09, 0.1 mg/g extract powder or more.

It is further understood that the utilized oly or its functionally related variant can be formulated or administered together with additional active ingredients as required to treat the condition of the patient.

Ostreolysin (Oly) is a protein found in the *Pleurotus ostreatus* mushroom (also known as oyster mushroom and Yarden mushrooms) and in *Pleurotus pulmonarious*. Oly a 15-kDa cytolytic protein expressed during fruiting bodies formation that may interact with cholesterol enriched domains.

The present invention is based on the surprising effects of oly and extracts comprising oly on in- vivo and in-vitro models and various parameters related metabolic syndrome and/or on fatty liver, obesity, over-weight, cancer and diabetes as well as the level of GOT, GPT, triglycerides and cholesterol.

Figure 12:
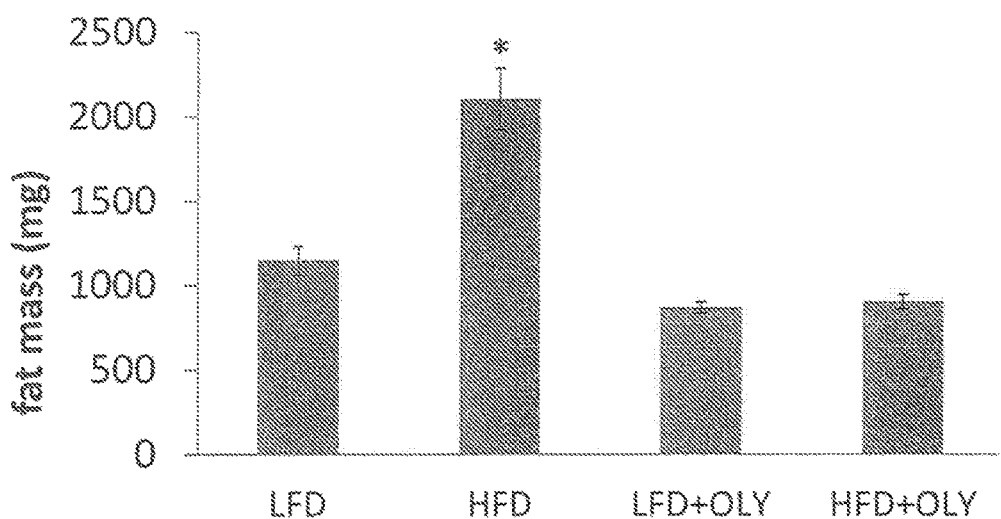
FIG. 12 is a graph representing the weight of epididymal adipose tissue on day of sacrifice *P<0.001 from HFD.

As clearly seen in the Examples section, low amounts of recombinant oly, as well as extracts comprising oly, showed a significant effect on lipid droplets accumulation in cells (FIG. 5), gene expression of adipogenesis markers (FIG. 6), weight gain (FIG. 8), IPGTT (FIG. 10), weight of epididimal adipose tissue (FIG. 12), liver weight and expression of genes (FIGS. 14 and 13, respectively) and other parameters like GOT, GPT, triglycerides and cholesterol.

As used herein, "Metabolic syndrome" or "syndrome X" is defined here on the basis of NCEP ATP III criteria, which are the presence of three or more of the following factors: 1) increased waist circumference (>102 cm [>40 in] for men, >88 cm [>35 in] for women); 2) elevated triglycerides (>150 mg/dl); 3) low HDL cholesterol (<40 mg/dl in men, <50 mg/dl in women); 4) non-optimal blood pressure (>130 mmHg systolic or mmHg diastolic); and 5) impaired fasting glucose (>110 mg/dl). It is to be understood that the method of the invention is intended for treating metabolic syndrome as defined herein as well as one or more of any one of the conditions of metabolic syndrome, separately or in combination defined herein or the complications described above.

As used herein, the term "fatty liver" refers to a condition where fat accumulates excessively in liver cells due to the disorder of lipid metabolism. It may cause various diseases such as angina, myocardial infarction, stroke, arteriosclerosis and pancreatitis.

"Impaired glucose tolerance" is defined here on the basis of American Diabetes Association criteria. Impaired glucose tolerance is two-hour 75-g oral glucose tolerance test values of 140 to 199 mg per dL (7.8 to 11.0 mmol/1).

"Impaired fasting glucose" is defined here on the basis of American Diabetes Association criteria. Impaired fasting glucose is defined as fasting plasma glucose values of 100 to 125 mg per dL (5.6 to 6.9 mmol/1).

"Diabetes Mellitus" generally refers to fasting plasma glucose values of equal or greater than 126 mg/dL (7.0 mmol/1).

"Insulin resistance" is defined here as a fasting blood insulin level greater than 20 mcU/mL.

"New onset diabetes" (usually defined on the basis of a fasting blood glucose concentration of 7.0 mmol/1 or more) in an individual.

"Hyperglycemia" is a fasting blood glucose concentration of 7.0 mmol/1 or greater.

Fatty liver, also known as fatty liver disease (FLD), is a reversible condition. Large vacuoles of triglyceride fat accumulate in liver cells via the process of steatosis (the abnormal retention of lipids within a cell). Fatty liver can be considered a single disease that occurs worldwide in those with excessive alcohol intake and the obese (with or without effects of insulin resistance). The condition is also associated with other diseases that influence fat metabolism. When this process of fat metabolism is disrupted, the fat can accumulate in the liver in excessive amounts, thus resulting in a fatty liver. Both alcoholic FLD from nonalcoholic FLD, have similar symptoms and are characterized by microvesicular and macrovesicular fatty changes at different stages.

Accumulation of fat may also be accompanied by a progressive inflammation of the liver (hepatitis), called steatohepatitis. Hepatic steatosis" refers to a process describing the abnormal retention of lipids within a hepatocyle. Fatty liver may be termed alcoholic steatosis or non-alcoholic fatty liver disease (NAFLD), depending on the alcohol consumption of the subject and the more severe forms as alcoholic steatohepatitis (part of alcoholic liver disease) and Non-alcoholic steatohepatitis (NASH).

For adults, "over-weight" and "obesity" ranges are determined by using weight and height to calculate a number called the "body mass index" (BMI). BMI is used because, for most people, it correlates with their amount of body fat. An adult who has a BMI between 25 and 29.9 is considered overweight. A BMI of 30 or higher is considered obese a BMI of 30 or higher is considered obese. All of these conditions or disorders are improved or treated by oly, oly related variant or a composition comprising an extract comprising oly, which may be mushroom extract and in some embodiments *Pleurotus* extracts.

As used herein, the term "oly" or "Ostreolysin" refers to the native Ostreolysin protein or to the recombinant Ostreolysin protein, comprising the amino acid sequence set forth in:

(SEQ ID NO: 1)
AYAQWVIIIIHNVGSQDVKIKNLKASWGKLHADGDKDAEVSASNYEGKII
KPDEKLQINACGRSDAAEGTTGTFDLVDPADGDKQVRHFYWDCPWGSKTN
TWTVSGSNTKWMIEYSGQNLDSGALGTITVDTLKKGN.

As used herein, the terms "fragment" or "oly fragment" refer to any amino acid sequence portion of oly.

As used herein, the terms "oly derivatives" or "oly analogs" refer to oly or oly fragment comprising at least one altered amino acid residue by an amino acid substitution, addition, deletion, or chemical modification, as compared with the sequence of oly or oly fragment. Oly derivatives include amino acid substitutions and/or additions with naturally occurring amino acid, with non-naturally occurring amino acid, with any chemically modified amino acid and with amino acid with any available molecular architecture.

As used herein, the phrase "oly functionally related variant" refers to any fragment, derivative or analog of oly or any combination thereof, having the same or enhanced functional activity of oly described herein.

In some embodiments of the invention, the oly functionally related variant have at least 70%, 75%, 80%, 85%, 90%, 95% or 99% sequence identity to the amino acid sequence set forth in SEQ ID NO. 1 or to the amino acid sequence of the oly protein.

In some embodiments of the invention, oly, oly fragments, oly derivatives, oly analogs or oly functionally related variant are isolated proteins. In some embodiments of the invention, oly, oly fragments, oly derivatives, oly analogs or oly functionally related variant are embedded in or connected to a carrier or molecular architecture of any type, size and atomic composition.

The improvement of a metabolically related parameter, metabolic associated disease and/or pathological condition related to metabolism, refers to one or more of the following (separately or in combination of one or more): reduction in weight, increase in energy consumption (possibly by increase in brown fat adipocytes production), improvement in liver related parameters, including liver mass, liver function (for example by improvement in the activity of liver enzymes such as GOT and GPT) and number of fatty droplets, improvement in clinical parameters associated with Non-alcoholic fatty liver disease (NAFLD), improvement in glucose related parameters, such as, blood/plasma glucose levels, improvement of glucose intolerance, and improvement in one or more parameters related to cholesterol, lipid, peptide, leptin and triglyceride levels.

It is known that NAFLD is the leading cause of chronic liver disease, wherein 20-30% of NAFLD patient progress to develop non-alcoholic steatohepatitis (NASH), which in turn can lead to cirrhosis, hepatocellular carcinoma and increased mortality, type II diabetes, hyperlipimedimia, hypercholesterolemia and diseases wherein a clinical beneficial effect is manifested by improvement of liver function or at least one related liver parameter. Thus, those conditions may also be treated by the method and the preparations of the present invention.

According to some embodiments, oly, its functionally related variant, or extract or mushroom extract comprising oly, its functionally related variant or a composition comprising oly or oly functionally related variant, or extract or mushroom extract comprising oly or composition extract or mushroom extract comprising oly may be used in the treatment of obesity, diabetes and/or complications thereof, possibly via promoting brown adipocyte differentiation and increasing energy expenditure. According to further embodiments, oly, its functionally related variant, or extract or mushroom extract comprising oly or a composition comprising oly, its functionally related variant, or extract or mushroom extract comprising oly may be used to improve liver function, reduce liver mass. According to some embodiments of the invention, oly, its functionally related variant, or extract or mushroom extract comprising oly or a composition comprising oly, its functionally related variant, or extract or mushroom extract comprising oly may be used to improve glucose intolerance in animals fed with a high fat diet. According to further embodiments, oly, its functionally related variant, or extract or mushroom extract comprising oly or a composition comprising oly, its functionally related variant, or extract or mushroom extract comprising oly are used to increase the metabolism of already fully differentiated adipocytes.

According to some embodiments of the invention there is provided a method of differentiating white adipocyte into brown adipocyte in a cell or inducing brown adipogenesis comprising contacting the cell with oly, oly functionally related variant or any combination thereof or an extract comprising oly. The method may be used for in-vitro tests, for example, without limitation for assessing synergistic effects between of oly and other active materials.

Further embodiments of the invention are directed to a method for increasing metabolic rate by contacting fat cells with an effective amount of oly, its functionally related variant, or extract or mushroom extract comprising oly or a composition comprising oly, its functionally related variant, or extract or mushroom extract comprising oly. According to some embodiments, the fat cells are brown, white or both. According to some embodiments, the higher metabolic rate can be caused by increased respiration and/or nutrient oxidation.

Further embodiments of the invention are directed to a method for enhancement of production of brown fat adipocytes the method comprising contacting a precursor of brown fat adipocytes with an effective amount of oly, its functionally related variant, or extract or mushroom extract comprising oly or a composition comprising oly, its functionally related variant, or extract or mushroom extract comprising oly.

Further embodiments of the invention are directed to methods of treating cancer comprising the administration of an effective amount of oly, its functionally related variant, or extract or mushroom extract comprising oly or a composition comprising oly, its functionally related variant, or extract or mushroom extract comprising oly. According to some embodiments, the treated cancer is colon cancer. According to other embodiments of the invention, the cancer is brain cancer, oropharyngeal cancer, nasopharyngeal cancer, renal cancer, biliary cancer, prostatic cancer, pheochromocytoma, pancreatic islet cell cancer, Li-Fraumeni tumors, thyroid cancer, parathyroid cancer, pituitary tumors, adrenal gland tumors, osteogenic sarcoma tumors, multiple neuroendrcine type I and type II tumors, breast cancer, lung cancer, head & neck cancer, prostate cancer, esophageal cancer, tracheal cancer, skin cancer brain cancer, liver cancer, bladder cancer, stomach cancer, pancreatic cancer, ovarian cancer, uterine cancer, cervical cancer, testicular cancer, colon cancer, rectal cancer or skin cancer. As used herein the term "cancer" refers to the presence of cells possessing characteristics typical of cancer-causing cells, for example, uncontrolled proliferation, loss of specialized functions, immortality, significant metastatic potential, significant increase in anti-apoptotic activity, rapid growth and proliferation rate, and certain characteristic morphology and cellular markers. Typically, the cancer cells are in the form of a tumor; existing locally within an animal, or circulating in the blood stream as independent cells, for example, leukemic cells. The treatment of cancer includes any reduction in the proliferation of cancer cells, as well as the prevention of the cancer from occurring, recurring, decreasing the growth rate, cessation of growth, tumor shrinkage, slowing the progression, decreasing metastasis, increasing survival rate, increasing quality of life of the cancer patients, and the like. The reduction of the proliferation of cancer cells may be achieved by decreased growth rates, cytostatic effects, cytotoxic effect, apoptotic effects, or any combination thereof.

In some embodiments, oly, its functionally related variant, or extract or mushroom extract comprising oly induce cell arrest and/or apoptosis. In some embodiments, oly, its functionally related variant, or extract or mushroom extract comprising oly induce cell arrest or apoptosis in a cancerous cell. In some embodiments, oly, its functionally related variant, or extract or mushroom extract comprising oly inhibit metastasis. In some embodiments, oly, its functionally related variant, or extract or mushroom extract comprising oly inhibit tumor growth. In some embodiments, oly, its functionally related variant, or extract or mushroom extract comprising oly inhibit angiogenesis. In some embodiments, oly, its functionally related variant, or extract or mushroom extract comprising oly inhibit cell cycle. In some embodiments, oly, its functionally related variant, or extract or mushroom extract comprising oly inhibit aberrant cell cycle.

According to some embodiments, the oly utilized according to the present invention is native oly, produced by mushrooms. According to some embodiments, the oly utilized according to the present invention is a recombinant protein. According to further embodiments, the oly is produced in a prokaryotic cell. According to some embodiments, the oly is produced in bacterial cells. According to some embodiments, the oly produced is not hemolytic. According to some embodiments, the bacterial cells are e. coli.

Some embodiments are directed to a pharmaceutical composition or a nutraceutical composition comprising as an active ingredient a therapeutically effective amount of oly, its functionally related variant, or extract or mushroom extract comprising oly, and a pharmaceutically or nutraceutically acceptable carrier. The present invention further provides a dietary supplement comprising oly or oly functionally related variant or an extract or a mushroom extract comprising oly. Pharmaceutically acceptable salts of the active ingredient (oly or a functionally related variant thereof) may also be used according to some embodiments. Pharmaceutically acceptable salts include those salts formed with free amino groups such as salts derived from non-toxic inorganic or organic acids such as hydrochloric, phosphoric, acetic, oxalic, tartaric acids, and the like, and those salts formed with free carboxyl groups such as salts derived from non-toxic inorganic or organic bases such as sodium, potassium, ammonium, calcium, ferric hydroxides, isopropylamine, triethylamine, 2-ethylamino ethanol, histidine, procaine, and the like.

The pharmaceutically or the nutraceutically composition comprising oly, its functionally related variant, or extract or mushroom extract comprising oly may comprise one or more additional active ingredient which is required to treat metabolic syndrome, or one or more of the metabolic syndrome conditions or complications described herein, as well as one or more of obesity, fatty liver, diabetes, cancer and high level of cholesterol and/or triglyceride. It is noted that the additional active ingredient may have synergistic effect with oly, oly, its functionally related variant, or with the extract or mushroom extract comprising oly.

The oly, its functionally related variant, or extract or mushroom extract comprising oly of the invention may also be prescribed to be taken in combination with other drugs used to treat obesity, lipodystrophy, appetite control in obesity, metabolic syndrome (as herein defined) as well as one or more of its conditions and/or complications (as herein defined) and lipodystrophy-related infertility or obesity, fatty liver, diabetes, cancer and high level of cholesterol and or triglyceride. When used in such combinations, the oly or its functionally related variant or extracts comprising oly and conventional drugs may be administered simultaneously, by the same or different routes, or at different times during treatment. The dose of the conventional drug selected will depend on the particular compound being used and the route and frequency of administration.

The invention also provides a pharmaceutical or nutraceutical pack or kit comprising one or more containers filled with one or more of the ingredients of the pharmaceutical or the nutraceutical compositions of the invention. Optionally associated with such container(s) is a notice in the form prescribed by a governmental agency regulating the manufacture, use or sale of pharmaceuticals or biological products, which notice reflects approval by the agency of manufacture, use or sale for human administration.

The term "pharmaceutically acceptable" means suitable for administration to a subject, e.g., a human. For example, the term "pharmaceutically acceptable" can mean approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the therapeutic compound is administered. Such pharmaceutical carriers can be sterile liquids, such as water and oils, including those of petroleum, animal, vegetable or synthetic origin, such as peanut oil, soybean oil, mineral oil, sesame oil and the like, polyethylene glycols, glycerine, propylene glycol or other synthetic solvents. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene glycol, water, ethanol and the like. The composition, if desired, can also contain minor amounts of wetting or emulsifying agents, or pH buffering agents such as acetates, citrates or phosphates. Antibacterial agents such as benzyl alcohol or methyl parabens; antioxidants such as ascorbic acid or sodium bisulfite; and agents for the adjustment of tonicity such as sodium chloride or dextrose are also envisioned.

The pharmaceutical or nutraceutical compositions or the dietary supplements can take the form of solutions, suspensions, emulsions, tablets, or capsules. The pharmaceutical compositions can also take the form of powders, gels, creams, ointments, foams, pastes, sustained-release formulations and the like. The compositions can be formulated as a suppository, with traditional binders and carriers such as triglycerides, microcrystalline cellulose, gum tragacanth or gelatin. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in: Remington's Pharmaceutical Sciences" by E. W. Martin, the contents of which are hereby incorporated by reference herein. Such compositions will contain a therapeutically effective amount of oly, its functionally related variant, e.g., in a substantially purified form, together with a suitable amount of carrier so as to provide the form for proper administration to the subject. In some embodiments of the invention, the nutraceutical or the dietary supplement may be added to a food such as a chewing gum, a dairy product or the like. In some embodiments of the invention, the nutraceutical or the dietary supplement may be added to liquid, such as water, milk or juice, The amount of oly, its functionally related variant, or extract or mushroom extract comprising the same, which will be effective in the treatment of a particular disorder or condition will depend on the nature of the disorder or condition, and can be determined by standard clinical techniques known to a person skilled in the art. In addition, in-vitro assays may optionally be employed to help identify optimal dosage ranges. The precise dose to be employed in the formulation will also depend on the route of administration, and the nature of the disease or disorder, and should be decided according to the judgment of the practitioner and each patient's circumstances. Effective doses can be extrapolated from dose-response curves derived from in-vitro or in-vivo animal model test bioassays or systems.

The route of administration of the pharmaceutical composition will depend on the patient, and/or disease or condition to be treated. Suitable routes of administration include, but are not limited to, parenteral administration, e.g., intradermal, intravenous, intramuscular, intralesional, subcutaneous, intrathecal, intraperitoneal, and any other mode of administration as known in the art. According to some embodiments, the composition is administered via oral, transdermal, rectal, vaginal, topical, nasal, inhalation and ocular modes of treatment. Pulmonary administration can also be employed, e.g., by use of an inhaler or nebulizer.

For oral applications, the pharmaceutical composition may be in the form of tablets or capsules, which can contain any of the following ingredients, or compounds of a similar nature: a binder such as microcrystalline cellulose, gum tragacanth or gelatin; an excipient such as starch or lactose; a disintegrating agent such as alginic acid, Primogel, or corn starch; a lubricant such as magnesium stearate; or a glidant such as colloidal silicon dioxide. When the dosage unit form is a capsule, it can contain, in addition to the ingredients of the above type, a liquid carrier such as fatty oil. In addition, dosage unit forms can contain various other materials which modify the physical form of the dosage unit, for example, coatings of sugar, shellac, or other enteric agents. The tablets of the invention can further be film coated.

The term "precursor of brown fat adipocytes" refers to any cell that can differentiate directly, or through intermediate cell types into brown fat adipocytes, including, for example, stem cells, mesenchymal stem cells, myogenic precursor, brown pre-adipocyte and white pre-adipocyte.

The terms "analog" and "derivative" refer to a peptide comprising at least one altered amino acid residue by an amino acid substitution, addition, deletion, or chemical modification, as compared with the native peptide. Peptide derivatives particularly include amino acid substitutions and/or additions with naturally occurring amino acid residues, and chemical modifications such as, for example, enzymatic modifications, typically present in nature. Peptide analogs particularly include amino acid substitutions and/or additions with non-natural amino acid residues, and chemical modifications which do not occur in nature.

The present invention encompasses the use of peptides/proteins of which at least one amino acid has been chemically modified. Chemical modifications of amino acid residues include, but are not limited to, amidation, methylation, acetylation, glycosylation, oxidation, reduction, myristylation, sulfation, acylation, ADP-ribosylation, cyclization, hydroxylation, iodination, derivatization by protecting/blocking groups, or any other derivatization method known in the art. Such alterations, which do not destroy, but may improve the biological activity of the oly.

In one embodiment, as used herein the terms "fragment" and "peptide" may be used interchangeably having all the same meanings and qualities.

In one embodiment, as used herein the terms "peptide" and "protein" may be used interchangeably having all the same meanings and qualities.

The derivatives, analogs, precursors, and fragments according to the principles of the present invention can also include side chain bond modifications, including but not limited to —CH2-NH—, —CH2-S—, —CH2-S=O, O=C—NH—, —CH2-O—, —CH2-CH2-, S=C—NH—, and —CH=CH—, and backbone modifications such as modified peptide bonds. Peptide bonds (—CO—NH—) within the peptide can be substituted, for example, by N-methylated bonds (—N(CH3)—CO—); ester bonds (—C(R)H—C—O—O—C(R)H—N); ketomethylene bonds (—CO—CH2-); α-aza bonds (—NH—N(R)—CO—), wherein R is any alkyl group, e.g., methyl; carba bonds (—CH2-NH—); hydroxyethylene bonds (—CH(OH)—CH2-); thioamide bonds (—CS—NH); olefinic double bonds (—CH=CH—); and peptide derivatives (—N(R)—CH2-CO—), wherein R is the "normal" side chain, naturally presented on the carbon atom. These modifications can occur at one or more of the bonds along the peptide chain and even at several (e.g., 2-3) at the same time.

The present invention also encompasses peptide/protein derivatives and analogs in which free amino groups have been derivatized to form amine hydrochlorides, p-toluene sulfonylamino groups, carbobenzoxyamino groups, t-butyloxycarbonylamino groups, chloroacetylamino groups or formylamino groups. Free carboxyl groups may be derivatized to form, for example, salts, methyl and ethyl esters or other types of esters or hydrazides, and amides. The imidazole nitrogen of histidine can be derivatized to form N-imbenzylhistidine.

Also included are those peptide/protein derivatives, which contain one or more naturally occurring amino acid derivatives of the twenty standard amino acid residues. For example: 4-hydroxyproline can be substituted for proline; 5-hydroxylysine can be substituted for lysine; 3-methylhistidine can be substituted for histidine; homoserine can be substituted or serine; and ornithine can be substituted for lysine. The peptide analogs can also contain non-natural amino acids. Examples of non-natural amino acids include, but are not limited to, sarcosine (Sar), norleucine, ornithine, citrulline, diaminobutyric acid, homoserine, isopropyl Lys, 3-(2'-naphtyl)-Ala, nicotinyl Lys, amino isobutyric acid, and 3-(3'-pyridyl-Ala).

Furthermore, the peptide/protein analogs can contain other derivatized amino acid residues including, but not limited to, methylated amino acids, N-benzylated amino acids, O-benzylated amino acids, N-acetylated amino acids, o-acetylated amino acids, carbobenzoxy-substituted amino acids and the like. Specific examples include, but are not limited to, methyl-Ala (MeAla), MeTyr, MeArg, MeGlu, MeVal, MeHis, N-acetyl-Lys, O-acetyl-Lys, carbobenzoxy-Lys, Tyr-O-Benzyl, Glu-O-Benzyl, Benzyl-His, Arg-Tosyl, t-butylglycine, t-butylalanine, phenylglycine, cyclohexylalanine, and the like.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant", including where the alteration results in the substitution of an amino acid with a chemically similar amino acid. Conservative substitution tables providing functionally similar amino acids are well known in the art. Guidance concerning which amino acid changes are likely to be phenotypically silent can also be found in Bowie et al., 1990, Science 247: 1306 1310. Such conservatively modified variants are in addition to and do not exclude polymorphic variants, interspecies homologs, and alleles. Typical conservative substitutions include but are not limited to: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, Proteins (1984)). Amino acids can be substituted based upon properties associated with side chains, for example, amino acids with polar side chains may be substituted, for example, Serine (S) and Threonine (T); amino acids based on the electrical charge of a side chains, for example, Arginine (R) and Histidine (H); and amino acids that have hydrophobic side chains, for example, Valine (V) and Leucine (L). As indicated, changes are typically of a minor nature, such as conservative amino acid substitutions that do not significantly affect the folding or activity of the protein.

As used herein, in one embodiment, the term "amino acid derivative" refers to a group derivable from a naturally or non-naturally occurring amino acid, as described and exemplified herein. Amino acid derivatives are apparent to those of skill in the art and include, but are not limited to, ester, amino alcohol, amino aldehyde, amino lactone, and N-methyl derivatives of naturally and non-naturally occurring amino acids. In an embodiment, an amino acid derivative is provided as a substituent of a compound described herein, wherein the substituent is —NH-G(Sc)—C(0)-Q or —OC(0)G(Sc)-Q, wherein Q is —SR, —NRR or alkoxyl, R is hydrogen or alkyl, Sc is a side chain of a naturally occurring or non-naturally occurring amino acid and G is C1-C2 alkyl. In certain embodiments, G is Ci alkyl and Sc is selected from the group consisting of hydrogen, alkyl, heteroalkyl, arylalkyl and heteroarylalkyl.

In some embodiments of the invention, the amino acids of the protein/peptide are of L or D stereoisomers or combination thereof.

As used herein, in one embodiment, the terms "peptide" or "protein" or "fragment" may be derived from a natural biological source, synthesized, or produced by recombinant technology. It may be generated in any manner, including by chemical synthesis. One or more of the amino acids may be modified, for example, by the addition of a chemical entity such as a carbohydrate group, a phosphate group, a farnesyl group, an isofarnesyt group, a fatty acid group, an acyl group (e.g., acetyl group), a linker for conjugation, functionalization, or other known protecting/blocking groups.

In one embodiment, peptide/protein of the present invention are purified using a variety of standard protein purification techniques, such as, but not limited to, affinity chromatography, ion exchange chromatography, filtration, electrophoresis, hydrophobic interaction chromatography, gel filtration chromatography, reverse phase chromatography, concanavalin A chromatography, chromatofocusing and differential solubilization.

In one embodiment, to facilitate recovery, the expressed coding sequence can be engineered to encode the peptide/protein of the present invention and fused cleavable moiety. In one embodiment, a fusion protein can be designed so that the peptide/protein can be readily isolated by affinity chromatography; e.g., by immobilization on a column specific for the cleavable moiety. In one embodiment, a cleavage site is engineered between the peptide and the cleavable moiety and the peptide can be released from the chromatographic column by treatment with an appropriate enzyme or agent that specifically cleaves the fusion protein at this site [e.g., see Booth et al., Immunol. Lett. 19:65-70 (1988); and Gardella et al., J. Biol. Chem. 265:15854-15859 (1990)].

In one embodiment, the protein/peptide of the present invention can also be synthesized using in-vitro expression systems. In one embodiment, in-vitro synthesis methods are well known in the art and the components of the system are commercially available.

In one embodiment, production of a protein/peptide of this invention is using recombinant DNA technology. A "recombinant" peptide, or protein refers to a peptide, or protein produced by recombinant DNA techniques; i.e., produced from cells transformed by an exogenous DNA construct encoding the desired peptide or protein.

In one embodiment, a peptide of this invention comprises at least 5 amino acids. In another embodiment, a peptide comprises at least 10 amino acids. In another embodiment, a peptide comprises at least 20 amino acids. In another embodiment, a peptide comprises at least 25 amino acids. In other embodiments, a peptide comprises at least 30 amino acids or at least 50 amino acids or 75 amino acids, or 100 amino acids, or 125 amino acids, or 150 amino acids, or 200 amino acids, or 250 amino acids or 300 amino acids or 350 amino acids or 400 amino acids. In one embodiment, a peptide of this invention consists essentially of at least 5 amino acids. In another embodiment, a peptide consists essentially of at least 10 amino acids. In other embodiments, a peptide consists essentially of at least 30 amino acids or at least 50 amino acids or 75 amino acids, or 100 amino acids, or 125 amino acids, or 150 amino acids, or 200 amino acids, or 250 amino acids or 300 amino acids or 350 amino acids or 400 amino acids. In one embodiment, a peptide of this invention consists of at least 5 amino acids. In another embodiment, a peptide consists of at least 10 amino acids. In other embodiments, a peptide consists of at least 30 amino acids or at least 50 amino acids or 75 amino acids, or 100 amino acids, or 125 amino acids, or 150 amino acids, or 200 amino acids, or 250 amino acids or 300 amino acids or 350 amino acids or 400 amino acids.

Natural aromatic amino acids, Trp, Tyr and Phe, may be substituted for synthetic non-natural acid such as TIC, naphthylelanine (Nol), ring-methylated derivatives of Phe, halogenated derivatives of Phe or o-methyl-Tyr.

As used herein, in one embodiment the term "amino acid" refers to naturally occurring and synthetic $\alpha$, $\beta$ $\gamma$ or $\delta$ amino acids, and includes but is not limited to, amino acids found in proteins, i.e. glycine, alanine, valine, leucine, isoleucine, methionine, phenylalanine, tryptophan, proline, serine, threonine, cysteine, tyrosine, asparagine, glutamine, aspartate, glutamate, lysine, arginine and histidine. In certain embodiments, the amino acid is in the L-configuration. Alternatively, the amino acid can be a derivative of alanyl, valinyl, leucinyl, isoleuccinyl, prolinyl, phenylalaninyl, tryptophanyl, methioninyl, glycinyl, serinyl, threoninyl, cysteinyl, tyrosinyl, asparaginyl, glutaminyl, aspartoyl, glutaroyl, lysinyl, argininyl, histidinyl, β-alanyl, β-valinyl, β-leucinyl, (β-isoleuccinyl, β-prolinyl, β-phenylalaninyl, β-tryptophanyl, β-methioninyl, β-glycinyl, β-serinyl, β-threoninyl, β-cysteinyl, β-tyrosinyl, β-asparaginyl, β-glutaminyl, β-aspartoyl, β-glutaroyl, β-lysinyl, β-argininyl or β-histidinyl. As used herein, in one embodiment the phrase "Conservatively modified variants" applies to both amino acid and nucleic acid sequences. "Amino acid variants" refers to amino acid sequences. With respect to particular nucleic acid sequences, conservatively modified variants refers to those nucleic acids which encode identical or essentially identical amino acid sequences, or where the nucleic acid does not encode an amino acid sequence, to essentially identical or associated (e.g., naturally contiguous) sequences. Because of the degeneracy of the genetic code, a large number of functionally identical nucleic acids encode most proteins. For instance, the codons GCA, GCC, GCG and GCU all encode the amino acid alanine. Thus, at every position where an alanine is specified by a codon, the codon can be altered to another of the corresponding codons described without altering the encoded polypeptide. Such nucleic acid variations are "silent variations", which are one species of conservatively modified variations. Every nucleic acid sequence herein which encodes a polypeptide also describes silent variations of the nucleic acid. One of skill will recognize that in certain contexts each codon in a nucleic acid (except AUG, which is ordinarily the only codon for methionine, and TGG, which is ordinarily the only codon for tryptophan) can be modified to yield a functionally identical molecule. Accordingly, silent variations of a nucleic acid which encodes a polypeptide is implicit in a described sequence with respect to the expression product.

In some embodiments, the invention further envisages inclusion of the oly or its functionally related variant or a fused protein thereof in a complex where it is attached to proteinaceous (e.g., heterologous amino acid sequence) or non-proteinaceous moieties (e.g., PEG), each of which being capable of prolonging the half-life of the composition while in circulation.

Such a molecule is highly stable (resistant to in-vivo proteaolytic activity, probably due to steric hindrance conferred by the non-proteinaceous moiety) and may be produced using common solid phase synthesis. Further recombinant techniques may still be used, whereby the recombinant peptide product is subjected to in-vitro modification (e.g., PEGylation as further described hereinbelow).

The phrase "non-proteinaceous moiety" as used herein refers to a molecule not including peptide bonded amino acids that is attached to the above-described IL-31amino acid sequence. According to some embodiments the non-proteinaceous moiety may be a polymer or a co-polymer (synthetic or natural). Non-limiting examples of the non-proteinaceous moiety of the present invention include polyethylene glycol (PEG) or derivative thereof, Polyvinyl pyrrolidone (PVP), divinyl ether and maleic anhydride copolymer (DIVEMA); polysialic acid (PSA) and/or poly (styrene comaleic anhydride) (SMA). Additionally, complexes which can protect oly or its functionally related variant from the environment and thus keep its stability may be used, including, for example, liposomes or micelles containing oly or its functionally related variant or a fused protein comprising thereof are also included in the invention.

According to some embodiments of the invention, the oly or its functionally related variant or the fused protein comprising oly or its functionally related variant of the invention are attached to a non-proteinaceous moiety, which may act as a sustained-release enhancing agent. Exemplary sustained-release enhancing agents include, but are not limited to hyaluronic acid (HA), alginic acid (AA), polyhydroxyethyl methacrylate (Poly-HEMA), glyme and polyisopropylacrylamide.

Attaching the amino acid sequence component of the oly or its functionally related variant or the fused protein comprising thereof of the invention to other non-amino acid agents may be by covalent linking or by non-covalent complexion, for example, by complexion to a hydrophobic polymer, which can be degraded or cleaved producing a compound capable of sustained release; by entrapping the amino acid part of the oly or its functionally related variant or the fused protein comprising thereof in liposomes or micelles to produce a complex comprising the oly or its functionally related variant or the fused protein comprising the same. The association may be by the entrapment of the amino acid sequence within the other component (liposome, micelle) or the impregnation of the amino acid sequence within a polymer to produce the final peptide of the invention.

In some embodiments, the PEG derivative is N-hydroxysuccinimide (NHS) esters of PEG carboxylic acids, succinimidyl ester of carboxymethylated PEG (SCM-PEG), benzotriazole carbonate derivatives of PEG, glycidyl ethers of PEG, PEG p-nitrophenyl carbonates (PEG-NPC, such as methoxy PEG-NPC), PEG aldehydes, PEG-orthopyridyl-disulfide, carbonyldimidazol-activated PEGs, PEG-thiol, PEG-maleimide. PEG-maleimide, PEG-vinylsulfone (VS), PEG-acrylate (AC) or PEG-orthopyridyl disulfide may be also used.

The non-proteinaceous moiety may be attached to the oly or its functionally related variant amino acid sequence in any chosen position, provided that the therapeutic activity of oly or its functionally related variant is retained.

In some embodiments of the invention, there is provided a fused protein that comprises oly or its functionally related variant and a protein that stabilizes oly or its functionally related variant or protect it in the blood stream or at the tissue. In some embodiments of the invention, there is provided a fused protein that comprises oly or its functionally related variant and IgG. The IgG may any subclasses or isotypes thereof, e.g., IgG1, IgG2, IgG3, IgG4.

In some embodiments of the invention, the oly or its functional related variant and IgG and the IgG and/or any other protein that may be used for extending the half-life of oly or its functional related variant and IgG in the serum are linked by a linker. In some embodiments of the invention, the linker is a sequence of between 2-20 amino acids.

In some embodiments of the invention, the linker is a sequence of between 4-12 amino acids which form a cleavage site for enzymes such as MMP9/2, trypsin, PSA, cathepsins, kallikreins, serine proteases, caspases and others. Additional possible cleavage sites are presented in CHOI et al., "Protease-Activated Drug Development", Theranostics, Vol. 2(2), pp. 156-178 (found in http://www.thno.org/v02p0156.pdf). In some embodiments, the linker is between 6-8 amino acids and in some embodiments includes a cleavage site for enzymes such as MMP9/2, trypsin, PSA, cathepsins, kallikreins, serine proteases, caspases and/or others.

In some embodiments, the linker that comprise a cleavage site of MMP-9/2, cathepsin ,trypsin, kallikreins, serine proteases, caspases or any other cleaving enzyme that can be added between oly or its functional related variant and IgG. In some embodiments, the invention provides a fused protein comprising oly or its functional related variant and IgG.

Furthermore, the present invention encompasses nucleic acids encoding the fusion proteins described herein. The invention further encompasses nucleic acids encoding oly or oly functionally related variant. In addition, vectors comprising these nucleic acids and cells transformed with such vectors are encompassed by the present invention.

In some embodiments of the invention an extract comprising oly may be used for treating the various conditions described herein, e.g. obesity, fatty liver, diabetes, cancer and the like. In some embodiments of the invention, the extract is a mushroom extract. The mushroom extract may be *Pleurotus ostreatus* extract. The extract may be prepared as detailed herein.

Dried powder may be prepared from fresh fruiting bodies of *Pleurotus ostreatus* (Yarden) mushrooms following freezing of fresh fruiting bodies with liquid nitrogen, lyophilizing and afterwards, grinding in in any appropriate grinder. Alternatively, the mushrooms are frozen at a temperature between −4° C. to −40° C., lyophilized and ground using any appropriate grinder. In some embodiments the grinding is performed for between about 20 seconds to 10 minutes. In some embodiments the grinding is performed for between about 30 seconds to two minutes. In some embodiments the grinding is performed for about one minute. The powdered fruiting bodies may be extracted with water, in some embodiments, cold water is used by stirring overnight or for a period of between about 20 minutes to 6 hours. The extract is then centrifuged at, for example, between about 3,000 rpm to 30 rpm for between about 10 min to two hours or more. The supernatant is filtered. Aliquots can be tested for Oly expression or activity in mouse HIB-1B cells.

As shown in Example 7, the freezing of fresh fruiting bodies with liquid nitrogen, followed by lyophiliziation and afterwards grinding provided higher oly concentration in comparison to mushrooms that were frozen at a temperature of about −20° C., lyophilized and grinded. However, the activity in mouse HIB-1B cells remained similar in aliquots from both preparations. In some embodiments of the invention, additional oly (which may be native or synthetic) may be added to the extract in order to provide an extract which is enriched by oly.

The following examples are presented in order to more fully illustrate certain embodiments of the invention. They should in no way, however, be construed as limiting the broad scope of the invention. One skilled in the art can readily devise many variations and modifications of the principles disclosed herein without departing from the scope of the invention.

EXAMPLES

Experimental Methods

Preparation of Ostreolysin

Figure 2:
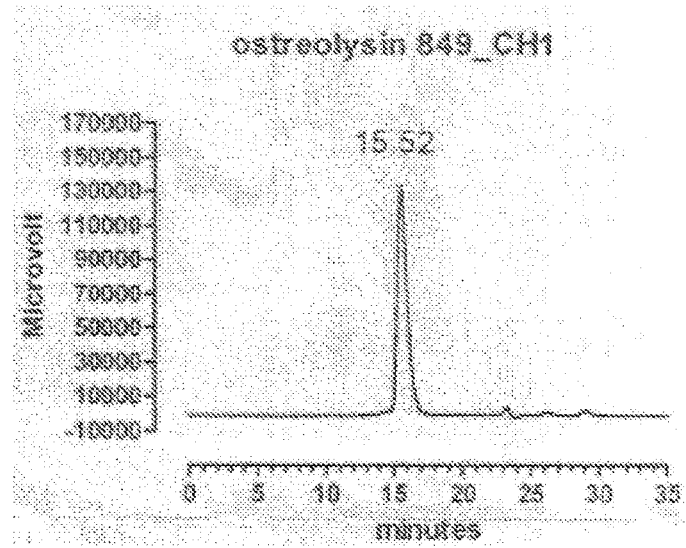
FIG. 2 presents gel filtration chromatography of oly on analytical Superdex 75 column, developed under non-denaturative conditions with 25 mM Tris-HCl+300 corresponding to the expected molecular size of a monomer.

Oly was PCR-amplified using primers containing the NcoI (at the 5' end) and BamHI+XbaI (at the 3' end) sites and subcloned to pTrc 99a vector at the NcoI and XbaI sites. Molecular mass of the protein was 15,400 Da, and the specific absorbance at 280 nm (calculated by DNAman program was 2.62 for g/L. The Protein was expressed upon induction with IPTG as soluble protein. The protein was purified by successive extraction, ammonium sulfate precipitation, dialysis, anion exchange chromatography, preparative gel filtration, dialysis and lyophilization in the presence of $NaHCO_3$ at approximate protein:salt ration of 1:1. Its concentration was calculated according to specific absorbance at 280 nm. The protein is easily soluble in DDW. Its purity was determined by SDS-PAGE in the presence of reducing agent (see FIG. 1) and by analytical gel filtration on Supperdex 75 column developed in the presence of 25 mM Tris-Hcl+300 mM NaCl, Ph 8 (see FIG. 2). The purity as determined by both methods was >95% and the molecular mass under non-denaturative conditions indicate that the protein is a monomer. In order to obtain high quantities of the oly, the protein was over expressed in *E. coli* and purified (see FIGS. 1 and 2).

Cell Cultures

HIB-1B brown pre-adipocytes [which are derived from a brown fat tumor of a transgenic mouse, and are the first established brown adipocyte cell line capable of expressing the brown fat-specific mitochondrial uncoupling protein (UCP)] were grown and differentiated or using rosiglitazone or treating them with Oly. Mouse 3T3-L1 were grown and differentiated with rosiglitazone.

RNA Extraction and RT-PCR

Total RNA was isolated using T-Reagent (Sigma). Reverse transcription was performed using High-Capacity cDNA (Applied Biosystems). RT-PCR was performed using SYBR Green (Applied Biosystems).

Western Blotting

Primary and secondary antibodies were obtained from Cell Signaling Technology (Danvers, Me.) or Santa Cruz Biotechnology (Santa Cruz, Calif.) and western blotting was performed as described in Yehuda-Shnaidman, E., et al., Acute stimulation of white adipocyte respiration by PKA-induced lipolysis. Diabetes, 2010. 59(10): p. 2474-83.

Immunofluorescence and Confocal Microscopy

Cells were seeded in 12-well plates, covered with glass cover slips and coated with 0.1% gelatin. A day later, oly (10-62.5 µg/ml) was added for 8h. Cells were fixed in 3.7% (v/v) PFA and permeabilized with 0.5% (v/v) Triton X-100 for three minutes. Cells were incubated with PFA 3.7% for 20 minutes and washed with PBS. After blocking for 1 h at room temperature with 5% (v/v) donkey serum, cover slips were incubated with caveolin-1 primary antibody (dilution 1:100) or oly primary antibody, over night at 40° C. Cover slips were washed with TBST and incubated with Alexa Fluor 488 goat anti-rabbit IgG secondary antibody and Phalloidin-TRITC for two hours at room temperature. Additional washes were performed and finally, mounting solution (70% (v/v)) containing DAPI (30% (v/v)) was added. Cells were observed under confocal Zeiss Axiovert 100M microscope (LSM 510, Germany).

Nile Red Staining

Cells were seeded onto 0.1% gelatin coated glass-bottom 24-well culture dishes (MatTak Corporation, Ashland, Me.). After overnight incubation at 37° C., 5% $CO_2$, cells were washed with PBS, incubated with 1 µg/ml nile red for 20 minutes at 37° C. and analyzed by confocal microscope.

Example 1

Figure 3:
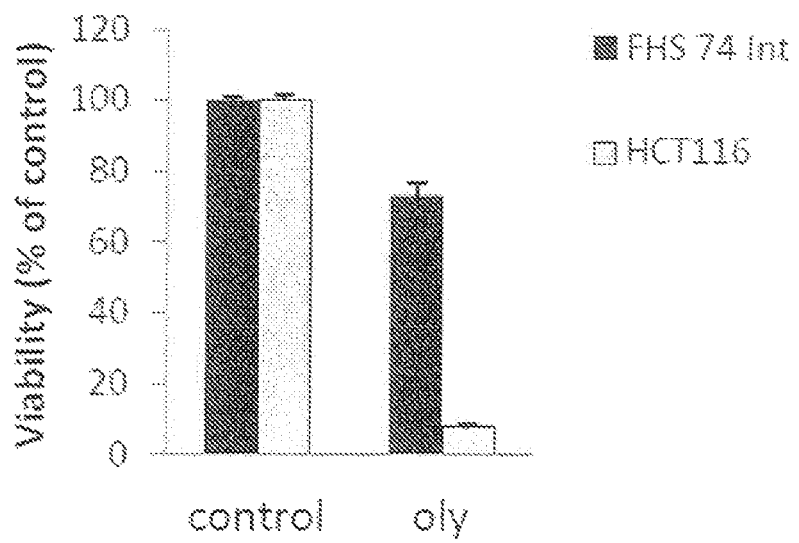
FIG. 3 is a graph presenting the cell viability of HCT116 and FHS 74 Int cell lines. Oly (62.5 µg/ml) was added for 24 hours and an MTT assay was performed.

In-Vitro Assay for Assessing the Anti-Proliferative Activity of the Recombinant Oly in HCT-116 Colon Cancer Cell Line Using a viability assay (MTT assay), the biological anti-proliferative activity of the recombinant oly in HCT-116 colon cancer cell line was tested. Similarly to the native protein, the recombinant oly has anti-proliferative activity (FIG. 3 gray). To further explore whether the anti-proliferative activity of oly is specific to cancer cells that possess high amounts of lipid drafts, the oly effect on the viability of non-cancer cell line, FHS 74 Int (human fetal small intestine), was tested. As shown in FIG. 3 (black column), the anti-proliferative activity of oly is much lower in the non-cancer cells (black) vs. the cancer cells (gray).

Example 2

Designation of a Polyclonal Specific Antibody Against the Whole Recombinant Oly

Figure 4:
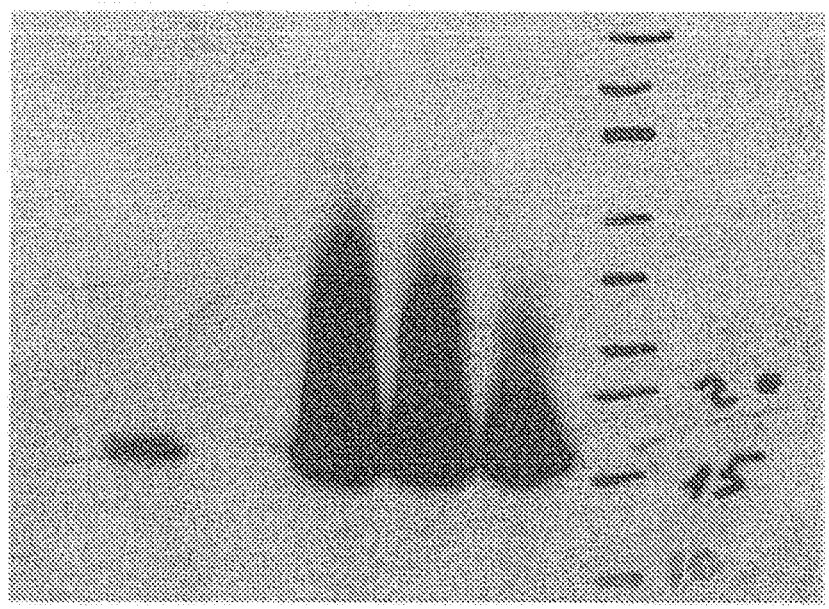
FIG. 4 Western blot analysis of oly using the newly designed polyclonal antibody. Proteins extracted from *P. ostreatus* fruiting bodies (50 µg, Fruiting Bodies (FB)) and the recombinant oly protein (2-4 µg) were loaded on SDS- PAGE and transferred into nitrocellulose membrane. The newly designed polyclonal antibody against oly was used (1:2,500 dilution).

A polyclonal specific antibody against the whole recombinant oly was designed. FIG. 4 demonstrates that the obtained antibody is highly oly-specific and recognizes both the recombinant and the wild type protein.

Example 3

An In-Vitro Assay for Testing the Role of Oly in Adipocyte Differentiation

Figure 5A:
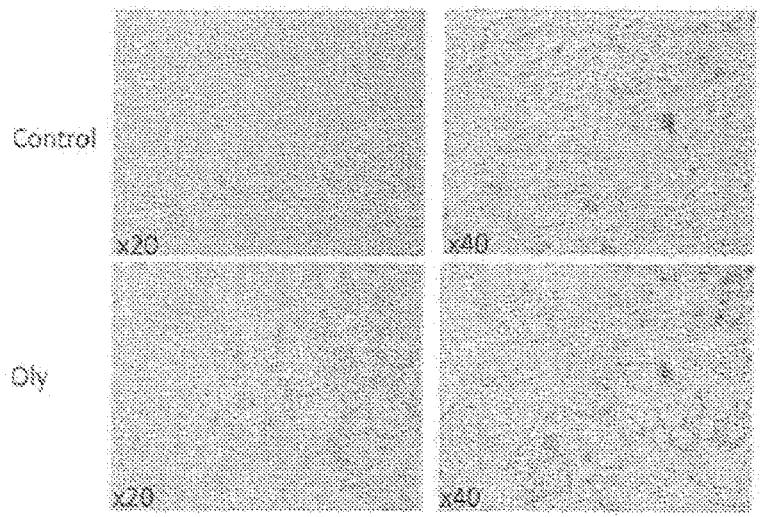
FIGS. 5A and 5B are microscopic images demonstrating lipid droplet accumulation in HIB-1B and 3T3-L1 cells. Particularly, FIG. 5A provides representative light microscopic images of oly-induced lipid accumulation in HIB-1B cells (10 μg/ml, 48 hours), wherein the upper images represent the control cells while the lower images represent the oly treated cells. Further, the left side images represent the ×20 magnification and the right side images are for the ×40 magnification.
Figure 5B:
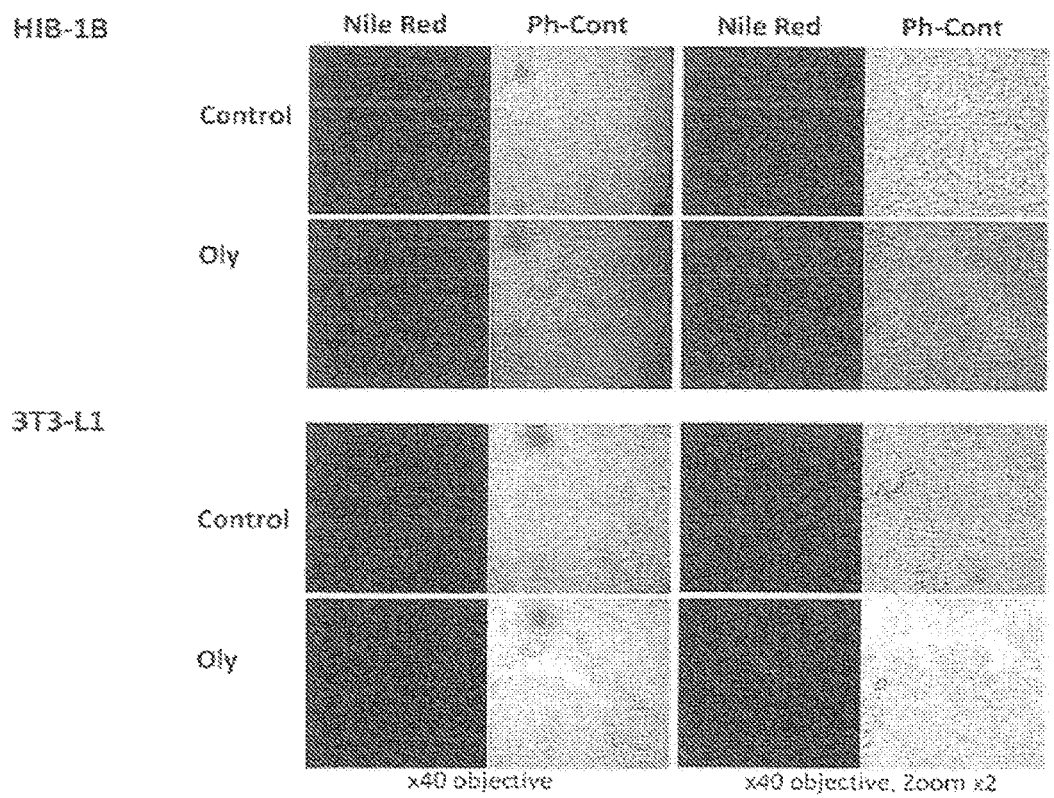

Once obtaining an active oly that can penetrate into cells, the oly was tested for its putative role in adipocyte differentiation. Mouse brown pre-adipocyte cell line, HIB-1B, and the mouse white pre-adipocyte cell line, 3T3-L1, were utilized in this test. When HIB-1B cells were treated with oly, morphological alterations were observed due to the accumulation of lipid droplets in the cytoplasm (FIG. 5A). This was also evidenced by Nile red staining (FIG. 5B). In contrast, oly-treated 3T3-L1 did not show lipid accumulation (FIG. 5B) but affected the gene expression of some differentiation genes (such as HSL and PGC-1α, not shown). Note: in both cell lines, best effect of oly was detected after 24-48 hours. Longer treatment periods did not result in additional changes.

Figure 6A:
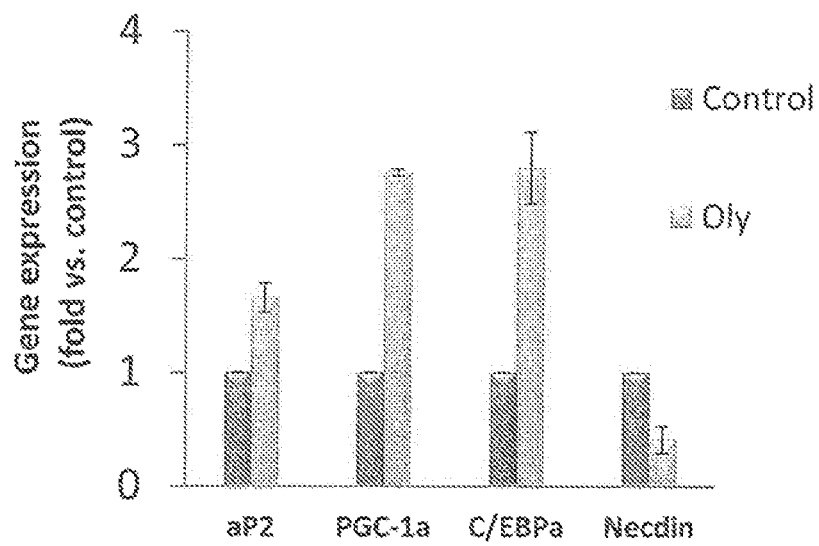
FIGS. 6A and 6B are graphs presenting the effects of oly (oly, 10 μg/ml, 48 hours) on the gene expression of adipogenesis markers (6A) and specific brown adipogenesis markers (6B). Gene expression was measured by Real Time-PCR and normalized to beta-actin.
Figure 6B:
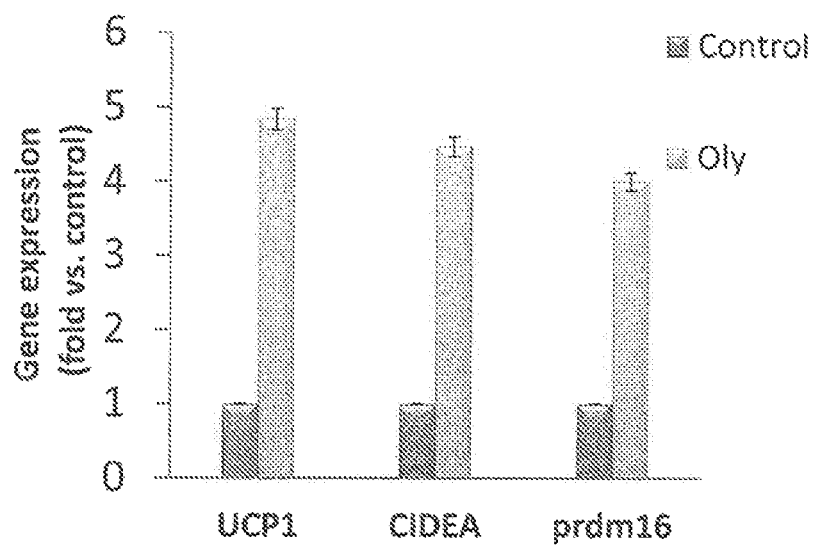

To further characterize oly-induced brown adipogenesis, the effect of oly on gene expression of some adipogenic markers was measured. FIG. 6A presents that oly induces an increase in the gene expression of aP2, PGC-1α and C/EBPα, while necdin (adipogenic inhibitor) is decreased, suggesting adipocyte differentiation. Moreover, oly increases the gene expression of specific brown adipogenesis markers, such as: UCP1, CIDEA and prdm16 (FIG. 6B). It is therefore hypothesized that oly induces differentiation of brown fat and that oly might lead to the transformation of white adipocytes into 'brown like' cells. It is known that white cells can transform into brown cells.

Figure 7:
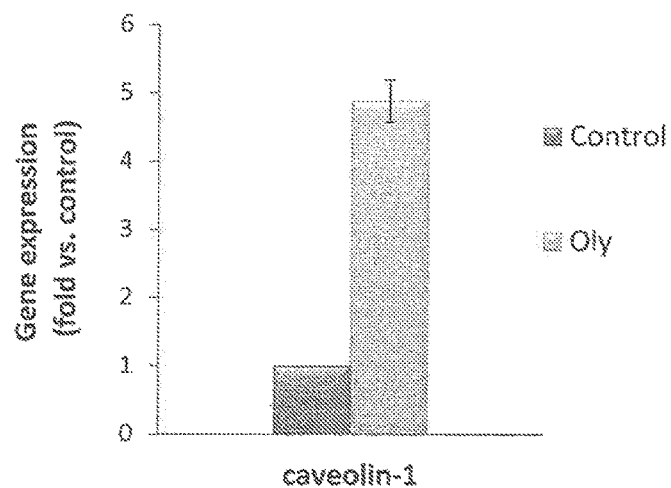
FIG. 7 is a graph presenting the oly-induced increase in the gene expression of caveolin-1. Gene expression was measured by Real Time-PCR and normalized to beta-actin. Oly treatment was 10 μg/ml, 48 hours.

The involvement of lipid rafts-related proteins in oly-induced brown adipogenesis was also explored. This question is especially relevant because of two reasons: (1) oly interacts with lipid rafts that in turn might lead to its entry through the cell membrane; (2) many accumulating evidences propose a role for caveolin-1 in adipocyte metabolism. Therefore, the role of caveolin-1 in oly-induced adipogenesis was tested. It was found that oly increases caveolin-1 gene expression in HIB-1B cells (FIG. 7). This suggests a role for caveolin-1 in oly effect and could be part of the differentiation process.

Example 4

In-Vivo Experiment of Toxicity

IP injection to mice of 0.2 mg/kg body weight (BW) or 0.5 mg/kg BW of recombinant oly did not induce mortality, nor any sign of sickness or toxicity in the injected mice, from the application following a week after administration.

Example 5

In-Vivo Tests for Assessing the Effect of Oly on Obesity, Diabetes and Fatty Liver Animals and Experiment's Design Male C57BL/6 mice, 5 weeks old, were purchased from Harlan laboratories, Ein Karem, Jerusalem. All mice were from the same litter. The mice were kept in four plastic cages in the same animal facility, each cage representing a different experimental group, wherein two groups were maintained on regular diet and two groups received high fat diet (60% of fat). Mice were given ad libitum access water. The mice were weighed twice a week. Following fourteen weeks during which the mice groups were provided the two different diet regimes, the injection period with oly started. The treatment groups (one cage of regular diet and one cage of high fat diet (HFD) mice were injected via the peritoneal cavity with a fixed concentration of oly (1.0 µg/gr BW) every other day; each mouse was weighed before the injection, and the injection volume of oly was adjusted according to the mouse's weight. Control groups were injected with similar volumes of saline. In all injections a sterile 1 ml syringe with 26 Ga ⅜" needle was used. Animal care and experimental procedures were in accordance with the accredited animal ethics committee of the Hebrew University.

Effect of Oly on Body Weight

Figure 8:
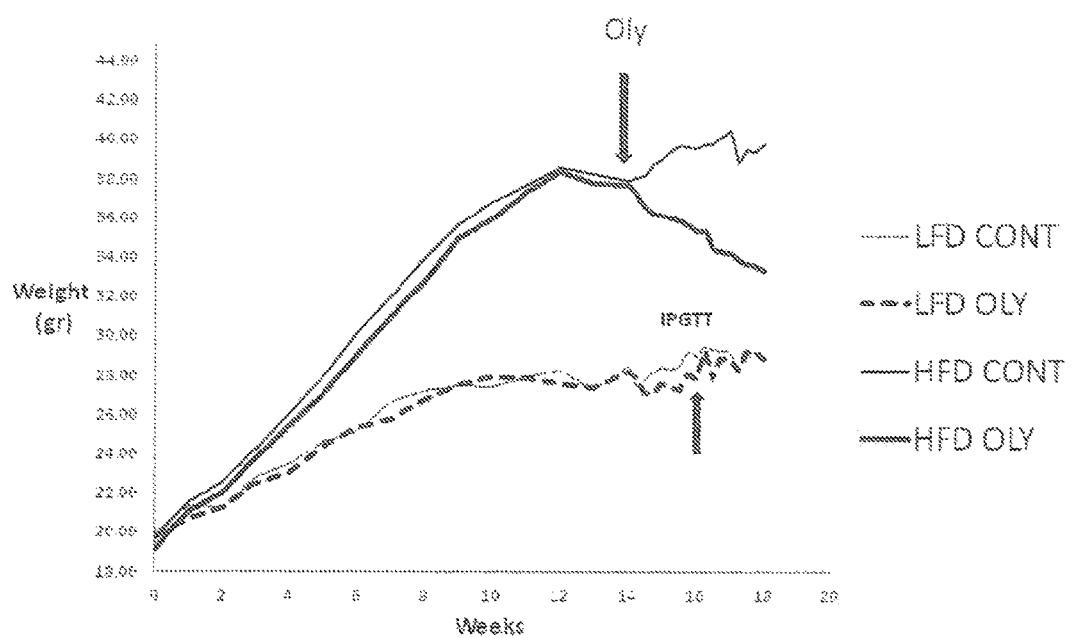
FIG. 8 is a graph representing the weight gain of mice submitted to the different dietary conditions (High Fat Diet (HFD) and Low Fat Diet (LFD)) and different oly treatments. IPGTT was conducted on week 16.
Figure 9:
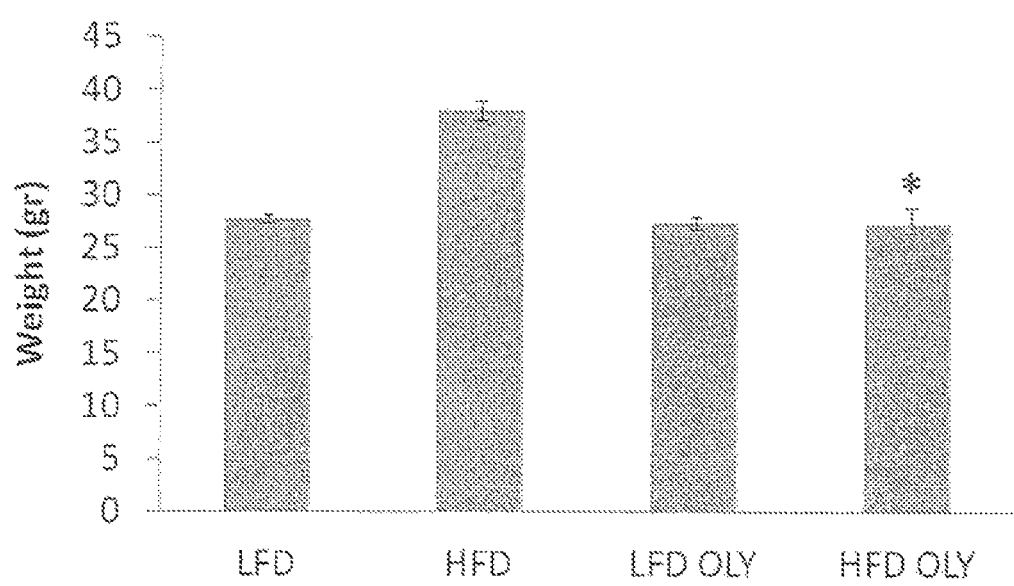
FIG. 9 is a graph representing the weight at the sacrifice day of mice exposed to the different dietary conditions and oly treatments. *P<0.05 from HFD.

The weight gain of the four groups of mice during the experiment is shown in FIG. 8, and FIG. 9 presents the weight of the mice on the day of sacrifice. The results show that oly administration to obese mice, i.e., those provided with a high fat diet, induced significant reduction in body weight.

Effect of Oly on Intraperitoneal Glucose Tolerance Test (IPGTT)

Figure 10A:
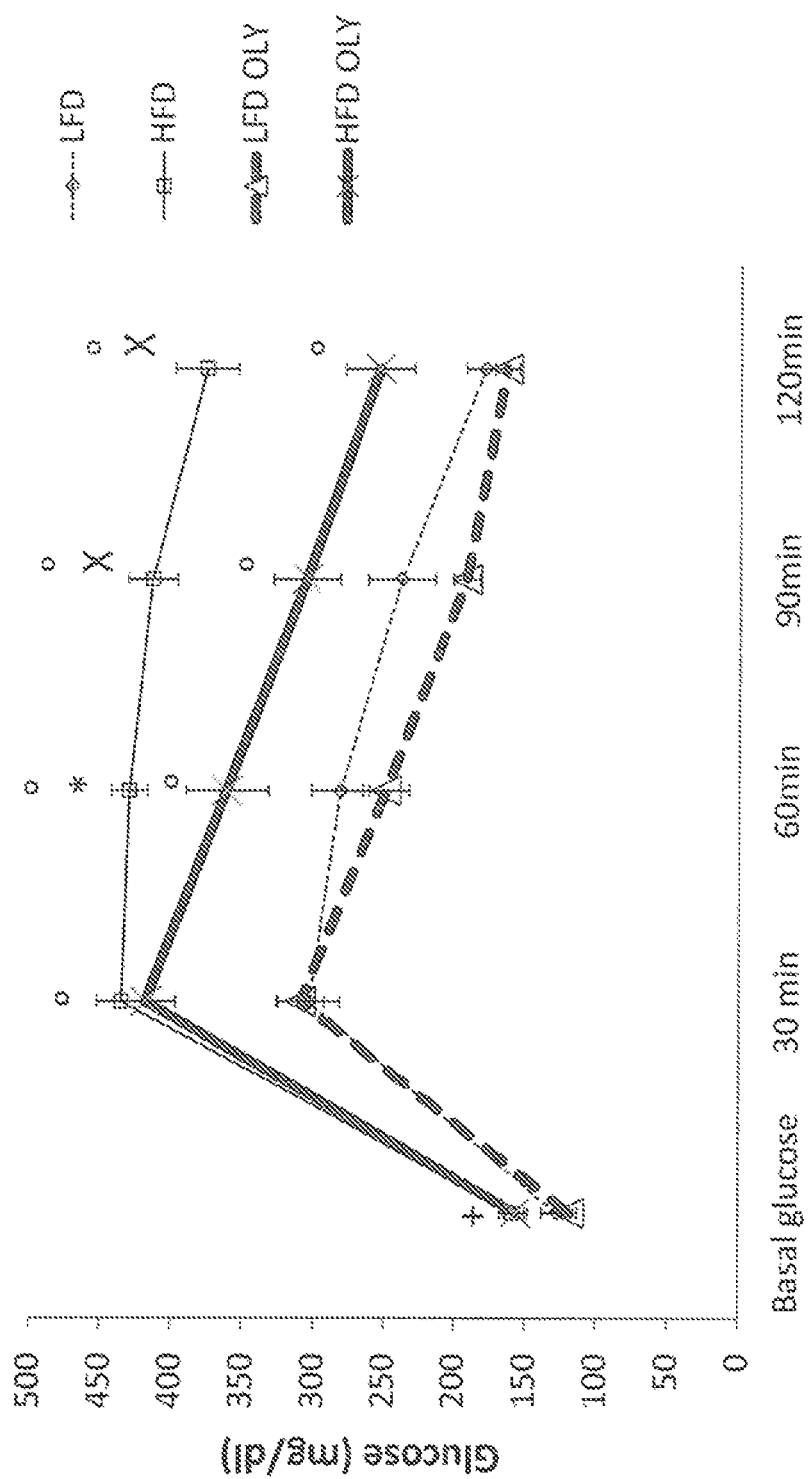
FIGS. 10A and 10B are graphs representing the results of intraperitoneal glucose tolerance test (IPGTT). (10A) Changes in blood glucose level of four experiment groups. (10B) Areas under the curve (AUC).
Figure 10B:
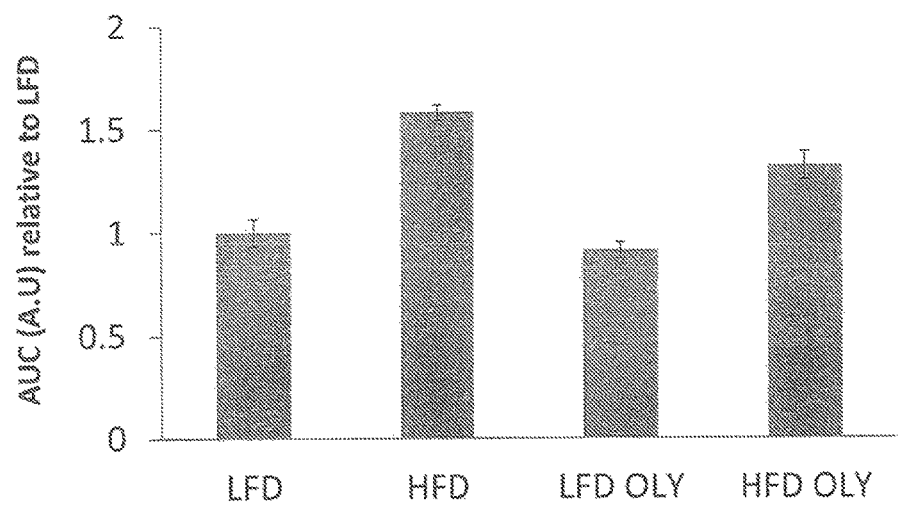

Fasting blood glucose levels were obtained from mice that fasted for 12 hours. The test was performed 16 weeks following day 1 of the experiment. Each mouse was weighed, and fasting glucose levels were obtained from venous blood from a small tail clip using a glucometer (Optimum Xceed, Abbot, UK) and respective blood glucose test strips (Optimum, Abbot, UK). Afterwards, glucose solution (20% (w/v) in saline) was injected using a 1 ml syringe, 26 Ga ⅜" needle, according to the mouse's weight (2 mg/gr body weight). Blood glucose levels were measured at 30, 60, 90 and 120 min after the glucose solution injection (see FIG. 10A). The area under the curve (AUC) of IPGTT was calculated representing the body's glucose tolerance for all mice groups (See FIG. 10B). As shown in FIGS. 10A and 10B, oly administration to obese mice induced significant reduction in glucose responsiveness, wherein oly significantly downregulated glucose intolerance.

Effect of Oly on Food Consumption

Figure 11:
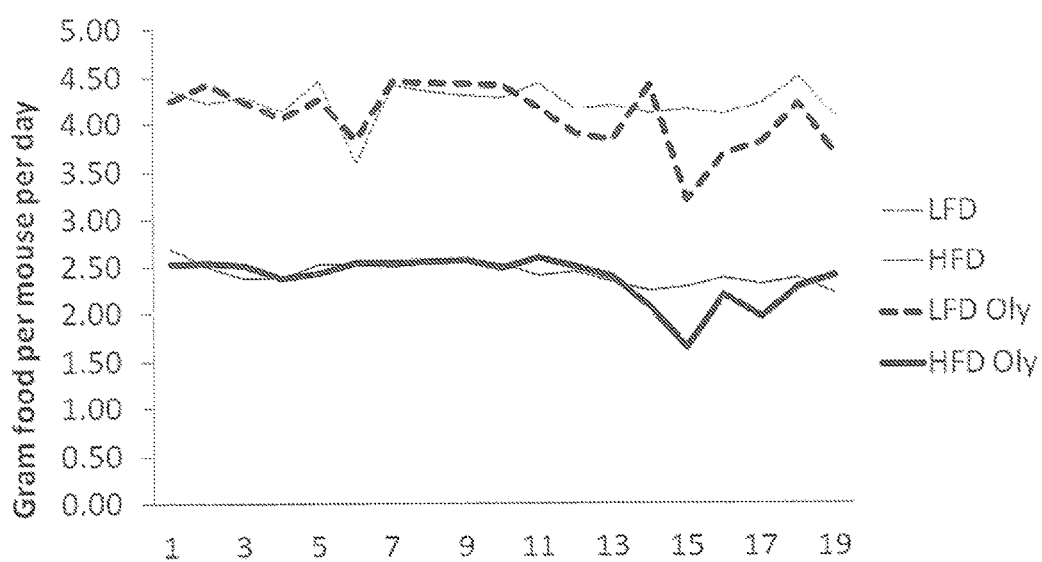
FIG. 11 is a graph representing the mouse food consumption.

The food consumption of the mice throughout the experiment was monitored and, as shown in FIG. 11, the food consumption of the mice is not affected by the administration of oly. Accordingly, the evidenced lowering in body weight is not due to lack of appetite or the like.

Effect of Oly on Body Tissues

Figure 13A:
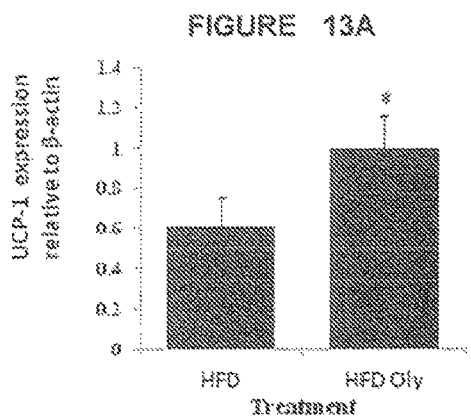
FIGS. 13A-D are graphs representing the expression of UCP-1 (13A), Cidea (13B), PRDM16 (13C), perilipin A relative to B-actin (13D)
Figure 13B:
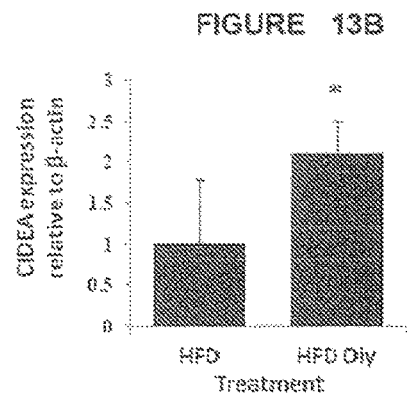
Figure 13C:
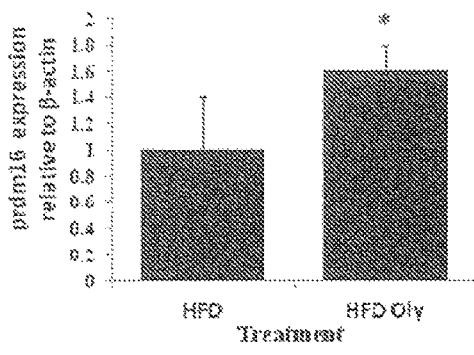
Figure 13D:
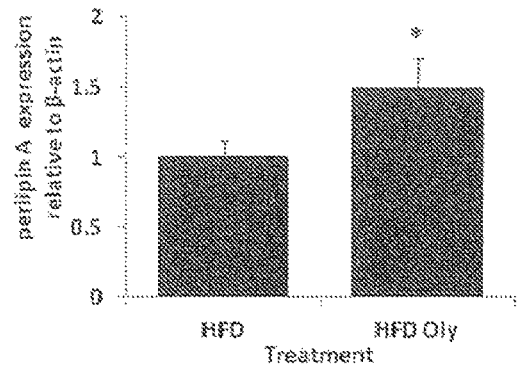
Figure 13E:
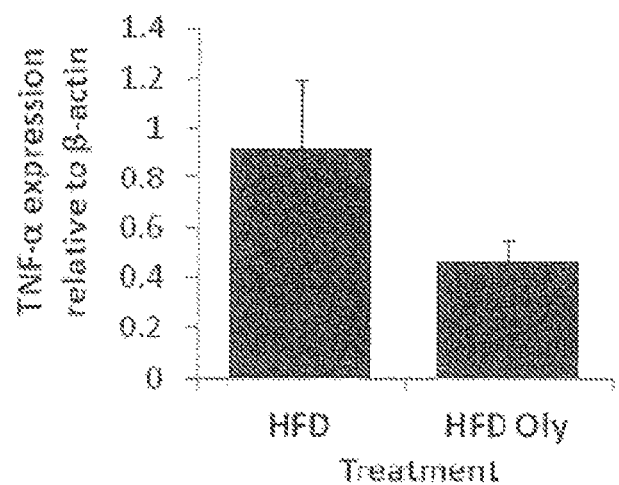
FIG. 13E is a graph representing the expression of TNF-α relative to β actin expression in visceral adipose tissue.

Following 20 weeks the mice of the different groups were sacrificed and different tissues analyzed as well as the blood samples. The weight of the epididymal adipose tissue is presented in FIG. 12. FIG. 13A presents the expression of UCP-1, Cidea, PRDM16, perilipin A (brown adipogenic markers), which, as shown therein, are upregulated by the administration of oly. The expression of TNF-α, on the other hand, was downregulated in the visceral adipose tissue by the administration of oly. It is therefore concluded that the administration of oly induced significant reduction in epididymal fat mass and controlled visceral mass towards a more brown-adipogenic characteristic.

Figure 14:
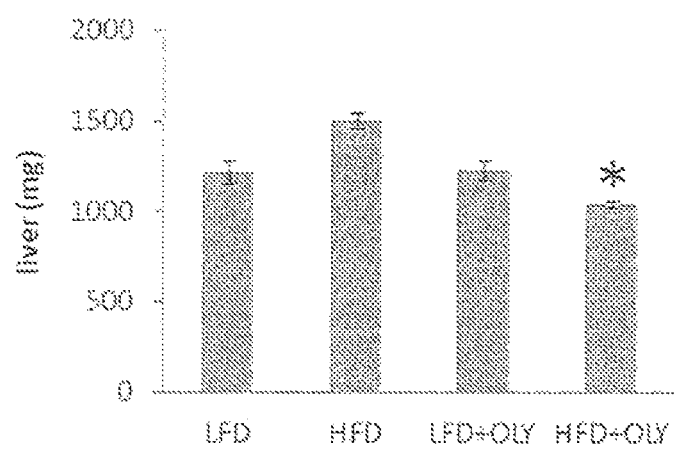
FIG. 14 is a graph representing the liver weights on day of sacrifice (P<0.05 from HFD group).
Figure 15:
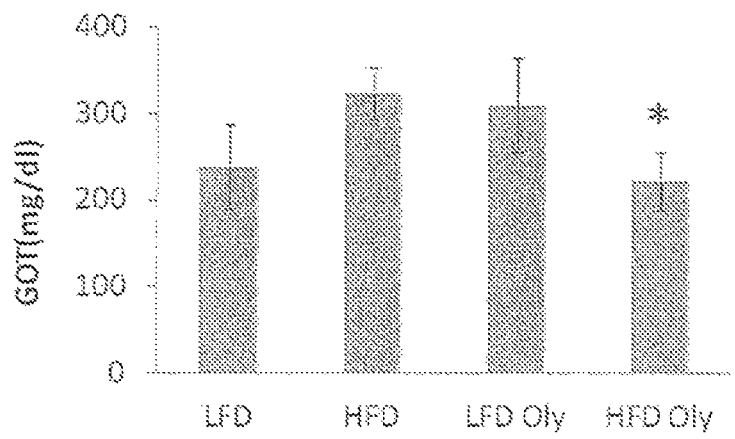
FIG. 15 is a graph representing the GOT levels on day of sacrifice (P<0.05 from HFD group).
Figure 16:
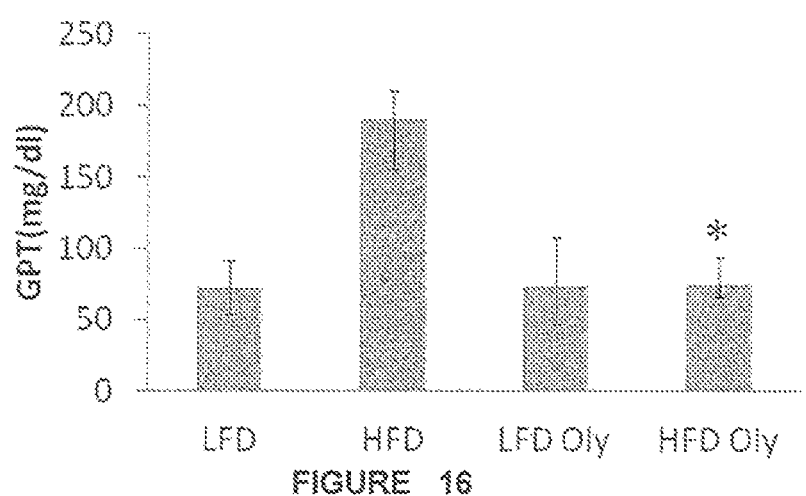
FIG. 16 is a graph representing the GPT levels on day of sacrifice (P<0.05 from HFD group).
Figure 17:
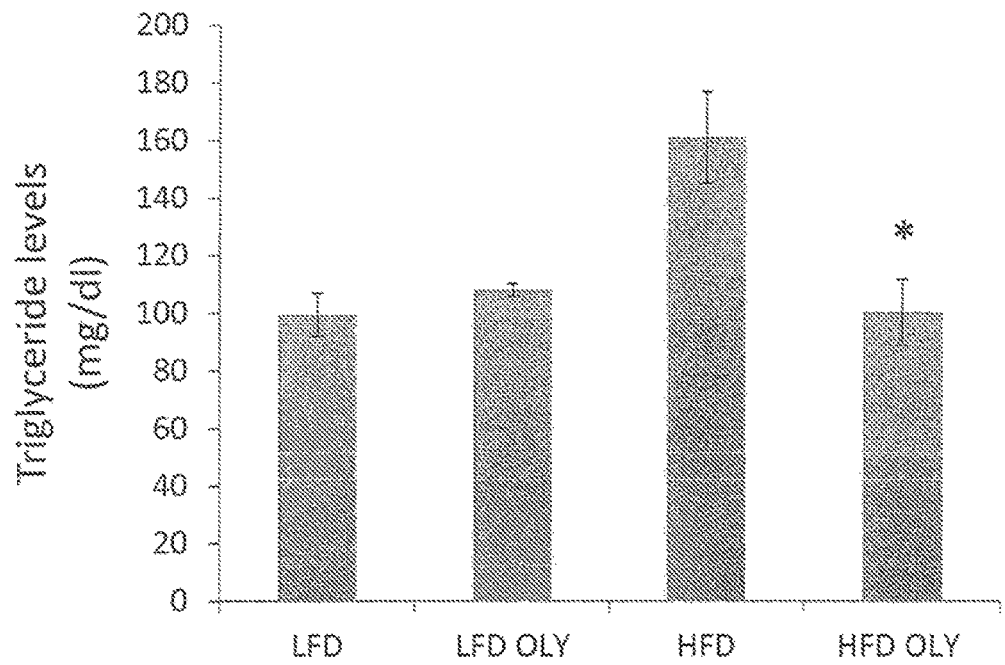
FIG. 17 is a graph representing the triglyceride levels on day of sacrifice (P<0.05 from HFD group).
Figure 18:
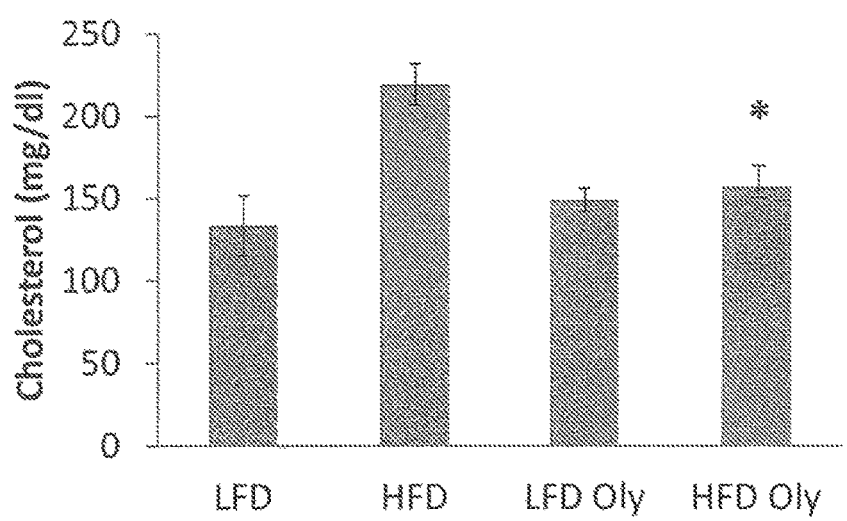
FIG. 18 is a graph representing the cholesterol levels on day of sacrifice (P<0.05 from HFD group).

FIG. 14 presents the liver weights of the mice on day of sacrifice, showing that the administration of oly induced a significant reduction in liver mass. Further, the blood was analyzed for liver functions, and, as shown in FIGS. 15 and 16, the transaminases GOT and GPT were significantly downregulated by the oly treatment. Further, as shown in FIGS. 17 and 18, the triglyceride and cholesterol levels were also significantly downregulated by the oly treatment.

In addition, the liver samples were tested histologically. As shown in FIG. 19, the livers of the mice provided with a high fat diet proved to be extremely fatty (see the control HF group), as apparent from the relatively high number of fatty droplets in comparison to the number of fatty droplets in the mice provided with a low fat diet. It further appears that the oly treatment reduced the fat levels in the liver, as apparent from the normal histological results obtain from the HFD mice treated by oly. The apoptosis in the livers was assessed as well. As presented in FIG. 20, oly downregulated the proapoptotic peptide Bax while upregulating the anti-apoptotic peptide Bcl2, and therefore BAX/BCL2 was downregulated in liver samples by the administration of oly, thus inhibiting the death of liver cells. The above results show that the administration of oly induced significant reduction in fatty liver appearance and associated liver activities.

In addition, various tests were conducted to assess the effect of Oly on Nonalcoholic fatty liver disease (NAFLD). The tests and the results are presented in Table 1 below.

TABLE 1

| | | Gene Expression (Arbitrary Units) | | | |
|---|---|---|---|---|---|
| Test | Explanation | Contol Diet (CD) | CD + Oly | HFD | HFD + Oly |
| Transcript expression of Cytosolic malic enzyme | Enzyme that generates NADPH used in fatty acid and cholesterol biosynthesis. Previous work has correlated liver and adipose malic enzyme expression with susceptibility to obesity and diabetes. Oly reduces the expression of this enzyme. | 0.48 ± 0.03 | 0.47 ± 0.03 | 0.26 ± 0.01 | 0.28 ± 0.01 Statistically Significant |
| Transcript expression of IRS2 | Hepatic insulin resistance and fatty liver is a critical component in the development of type 2 diabetes mellitus. Insulin resistance in liver is associated with reduced expression of both major insulin receptor substrate (IRS) proteins, IRS-1 and IRS-2. Oly sensitizes the liver to insulin by upregulating IRS2. | 0.18 ± 0.02 | 0.19 ± 0.03 | 0.10 ± 0.01 | 0.14 ± 0.02 Statistically Significant |
| Transcript expression of FASN | Fatty acid synthase (FASN) catalyzes the last step in fatty acid biosynthesis, and is a major determinant of the maximal hepatic capacity to generate fatty acids by de novo lipogenesis. FASN mRNA expression in human control vs NAFLD livers confirmed significantly higher FASN levels in hepatic steatosis. Oly downregulates FASN expression. | 0.10 ± 0.05 | 0.08 ± 0.02 | 0.14 ± 0.01 | 0.11 ± 0.02 Statistically Significant |
| Transcript expression of LPL | Tissue-specific overexpression of lipoprotein lipase (LPL) causes tissue-specific insulin resistance. It happens in fatty liver. Oly inhibits expression of this enzyme. | 0.12 ± 0.03 | 0.08 ± 0.02 | 0.14 ± 0.01 | 0.125 ± 0.02 Statistically Significant |
| Transcript expression of PKLR | PKLR is the protein encoded by the gene pyruvate kinase that catalyzes the transphosphorylation of phohsphoenolpyruvate into pyruvate and ATP, which is the rate-limiting step of glycolysis. It provides the substrate for glycerol and fatty acid accumulation in the liver. Oly inhibits expression of this enzyme. | 0.14 ± 0.04 | 0.08 ± 0.01 | 0.19 ± 0.02 | 0.09 ± 0.01 Statistically Significant |
| Transcript expression of IKKE | IKKE and TBK1 are part of a process of inflammation linked to obesity and insulin resistance, the condition that precedes Type 2 diabetes. Oly downregulates them. | 0.01 ± 0.001 | 0.01 ± 0.002 | 0.035 ± 0.003 | 0.01 ± 0.001 Statistically Significant |

TABLE 1-continued

| Test | Explanation | Gene Expression (Arbitrary Units) | | | |
| --- | --- | --- | --- | --- | --- |
| | | Control Diet (CD) | CD + Oly | HFD | HFD + Oly |
| Transcript expression of TBK1 | IKKE and TBK1 are part of a process of inflammation linked to obesity and insulin resistance, the condition that precedes Type 2 diabetes. Oly downregulates them. | 0.09 ± 0.01 | 0.07 ± 0.02 | 0.11 ± 0.01 | 0.06 ± 0.01 Statistically Significant |
| Transcript expression of CCL2 or MCP-1 | CCL-2 or MCP-1 play a significant role in hepatic steatosis or early liver injury. | 0.04 ± 0.01 | 0.05 ± 0.01 | 0.19 ± 0.02 | 0.06 ± 0.01 Statistically Significant |
| Transcript expression of CCL3 | CCL3 is elevated in the plasma and metabolic tissues (liver and adipose tissue) of patients with hyperlipidemia and metabolic disease. Thus CCL3 is an important chemokine in recruitment of immune cells to metabolic tissues. Oly downregulates its expression | 0.9 ± 0.1 | ND | 2.4 ± 0.3 | 0.4 ± 0.05 Statistically Significant |
| Transcript expression of EMR1 | EMR1 or EGF-like module containing mucin-like hormone receptor-like 1 [EMR1] is a marker of inflammation in the liver, downregulated by Oly | 0.041 ± 0.01 | 0.041 ± 0.01 | 0.05 ± 0.02 | 0.038 ± 0.01 Statistically Significant |

Example 6

Effect of Oly in Cancer

Methods
Cell Lines and Culture Conditions

HCT116 colorectal carcinoma cells (ATCC number: CCL-247) were maintained in Dulbecco's modified Eagle's medium (DMEM; Sigma-Aldrich, Israel) supplemented with 10% (v/v) Fetal bovine serum (FBS; Biological Industries, Beit Haemek, Israel) and 0.2% (v/v) penicillin-streptomycin-nystatin. HM7 highly metastatic colon cancer cells from clone #1 (HM7 cells transfected with pcDNA3 neo plasmid, not expressing Caveolin-1) and clone #15 (HM7 cells transfected with pcDNA-Caveolin-1, Plasmid with Caveolin-1 protein insert, expressing high levels of Caveolin-1) were maintained in DMEM supplemented with 10% (v/v) FBS and 0.275% (v/v) G-418 (Gibco, Paisley, UK). All cells were cultured in 5% $CO_2$ in a humidified atmosphere at 37° C.

Anti-cancer Activity (MTT Assay) HCT116 cells and HM7 cells from clone #1 and clone #15 were seeded in 96-well plate ($2.0 \times 10^4$ per well). After pre incubation over night at 37° C. in a $CO_2$ incubator, the recombinant protein Ostreolysin, prepared by expression in E. coli, was added to cell cultures at a concentration of 125 µg/ml and 62.5 µg/ml. Fresh medium alone was added to the control. Fruiting body extract was added at three concentrations: 0.01% (w/v), 0.025% (w/v), 0.05% (w/v). After incubation for 4, 8, 12, 24 hours at 37° C., medium was removed and 50 µl of 3-(4-, 5-dimethyl-2-thiazolyl)-2,5-diphenyltetrazoliumbromide (MTT) solution (0.5 mg/ml) was added. The plates were incubated for 1 hr at 37° C. After MTT solution was removed, 100 µl DMSO were added to each well and the plates were shaken for 20 min. Formation of colored formazan was assessed at 550 nm in ELx 808 Ultra microplate reader (BIO-TEK INSTRUMENTS INC) using KC junior software.

Cell Cycle Analysis

HCT116 cells were plated in 6-well plates ($9.0 \times 10^5$ cells per well) and allowed to adhere overnight. Fresh medium was added to the cell culture with the recombinant protein Ostreolysin at a concentration of 125 µg/ml. Fresh medium alone was added to the control. Fruiting body extract was added at a concentration of 0.01% (w/v). After 8 hours incubation, the cells were washed in PBS, trypsinized, harvested and re-suspended in 0.5 ml sterile PBS. 0.5 ml of cold 70% (v/v) ethanol was added to cell suspensions while vortexing and the samples were stored at 4° C. For staining, cells were centrifuged for 5 min at 1500 rpm (Hettich Zentrifugen Rotofix 32), the upper layer was discarded and DNA fragmentation solution (0.05 mg/ml propidium iodide, 0.1% (v/v) Triton X-100 and 0.1% (w/v) sodium citrate) was added for 1 hour incubation on ice. The DNA content was measured by exciting propidium iodide at 488 nm and measuring the emission at 575 nm (FL2) using a flow cytometer (BD FACScalibur BD Biosciences, San Jose, Calif.). Analysis was performed by WinMDI 2.9 software.

Western Blotting and Densitometry

HCT116 cell lysates were, electrophoresed in 12% SDS-PAGE, transferred to nitrocellulose transfer membranes (Whatman, Schleicher, Schuell, Dassel, Germany), blocked in TBST containing 5% (w/v) dry nonfat milk and incubated with PARP-1 (dilution 1:1000) or BAX (1:500) or β-actin (dilution 1:10,000) antibody over night at 4° C. Membranes were subsequently incubated with a secondary anti-rabbit antibody coupled to horseradish peroxidase (Jackson IR, Baltimore, Pa., USA, dilution 1:10,000) for 1 hour at room temperature. Proteins were visualized using an ECL kit. Effective transfer to nitrocellulose membrane was confirmed by staining with Ponceau S. Films were scanned by a Mustek 1200 UB Plus scanner (Mustek systems Inc., CA, USA). Densitometry was assessed using the Gelpro32 analyzer software and β-actin was used as a loading control.

Immunofluorescence and Confocal Microscopy

HCT116 cells were seeded at a density of $3.6 \times 10^5$ cells per well on glass cover slips (diameter, 1.8 cm) coated with 0.1% gelatin, placed in 12-well plates. The cells were allowed to adhere over night and treatments were applied as follows: Fresh medium was added to cell culture with the recombinant protein oly at a concentration of 125 μg/ml. Fresh medium alone was added to the control. Fruiting body extract was added at a concentration of 0.01% (w/v). After 4 or 8 hours incubation, the cells were fixed with 3.7% (v/v) PFA and permeabilized with 0.5% (v/v) Triton X-100 for 3 min. Afterwards, the cells were incubated with PFA 3.7% for 20 min and washed three times with PBS. To block unspecific staining, the cells were incubated for 1 hr at room temperature with 5% (v/v) donkey serum in TBST. The cells were sequentially stained with Caveolin-1 primary antibody (dilution 1:100) or Ostreolysin primary antibody (dilution 1:500) or Flotillin-1 primary antibody (dilution 1:100) in a humidity chamber over night at 4° C. Cover slips were washed three times for 30 min with TBST and then incubated with Alexa Fluor 488 goat anti-rabbit IgG secondary antibody (dilution 1:500) and Phalloidin-TRITC in a humidity chamber for two hours at room temperature. Cover slips were washed four times with TBST and then mounted upside-down with mounting solution (70% (v/v)) mixed with mounting solution with DAPI (30% (v/v)) on glass slides. The cells were observed under Leica CTR4000 Confocal microscope (Mannheim, Germany) at ×63 magnification using immersion oil.

Results

Recombinant Ostreolysin Exerts an Anti Proliferative Effect on HCT116 Cells and HM7 Clones Exposure of HCT116 (colorectal carcinoma cells) to oly has shown cytotoxicity with an effective concentration of 125 μg/ml producing a 50% decrease in cell viability at 8 hours (FIG. 21C). The cytotoxic effect of oly was also observed in HM7 (highly metastatic colon cancer). HM7 clone #15 (expressing high Cav-1 levels) presented a significant increased sensitivity to oly as compared with clone #1 (no Cav-1 expression) when administered for 4 and 8 hours (FIGS. 21B and 21D, respectively).

Direct microscope observation of cell morphology confirmed that oly had a similar effect on HCT116 cell line and HM7 clones, producing shrinkage of cells (data not shown). The cytotoxic activity of oly had already peaked after 4 hours of incubation in both cell lines.

In order to test whether the cytotoxic effect of oly is specific to cancer cells, the oly effect on the viability of non-cancer cell line, FHS 74 Int (human fetal small intestine) was also tested. As seen in FIG. 3 (see in Example 1), the anti-proliferative activity of oly is much lower in the normal cells (FHS 74 Int, black) vs. the cancer cells (HCT116, gray), implying a specific anti-proliferative role for oly in cancer cells.

Figures 22A, 22B:
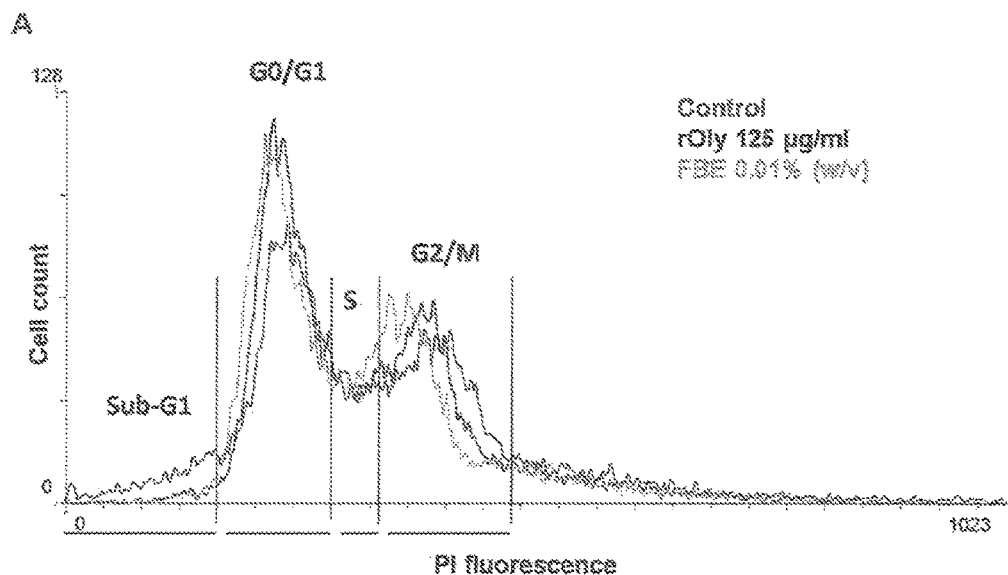
FIG. 22A and FIG. 22B show fluorescence activated cell sorting analysis of HCT116 cell line. Particularly.

Cell Cycle Analysis of HCT116 Cell Line Indicated that Recombinant Oly Induces Apoptosis in These Cells In order to quantify cell distribution in apoptosis and cell cycle, HCT116 cell line was analyzed by flow cytometry (FIG. 22A) without treatment (control) or with oly 125 μg/ml and FBE 0.01% (w/v). After staining with a quantitative DNA-binding dye, cells that have lost DNA via apoptosis will take up less stain and will appear as a sub-G1 peak to the left of the G1 peak. The results demonstrate that in HCT116 untreated cells, cell cycle distribution was 1.238±0.124, 42.482±1.709, 13.198±0.845, 27.997±0.856 in apoptosis, G0/G1, S, G2/M respectively. In HCT116 cells treated with FBE 0.01% (w/v) cell cycle distribution was 2.045±0.326, 33.807±1.109, 11.483±0.726, 27.560±1.102 in apoptosis, G0/G1, S, G2/M respectively. In HCT116 cells treated with oly 125 μg/ml cell cycle distribution was 7.380±0.584, 46.048±2.307, 13.022±1.158, 25.988±0.487 in apoptosis, G0/G1, S, G2/M respectively. The differences between untreated HCT116 cells and oly 125 μg/ml treated HCT-116 cells were significant with P-value of <0.05 (FIG. 22B).

Recombinant Ostreolysin Promotes the Cleavage of PARP-1 and Expression of BAX Pro-apoptotic Markers in HCT116 Cell Line (Colon Cancer Human Cell Line)

Figure 23A:
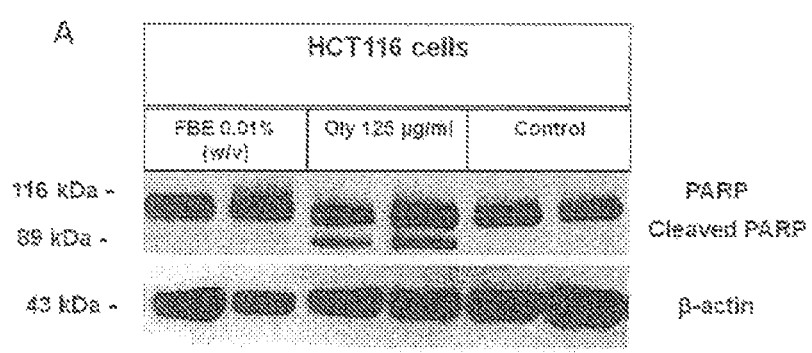
FIG. 23A: Data shown are representative of one out of three independent experiments, each performed in duplicates.

The extent of apoptosis was assessed by detection of active PARP-1 and detection of BAX protein using western blot. PARP, a 116 kD nuclear poly (ADP-ribose) polymerase is one of the main cleavage targets of caspase-3 in- vivo. Cleavage separates the PARP amino-terminal DNA binding domain (24 kD) from the carboxy-terminal catalytic domain (89 kD) (10) and serves as a marker of cells undergoing apoptosis. In HCT116 cell line, oly 125 μg/ml treatment induced cleavage of PARP (FIG. 23A), revealed by an antibody that recognizes both the full-length 116 kD fragment as well as the 89 kD cleaved fragment. BAX is a 23 kD pro-apoptotic protein, member of the Bcl-2 family. The critical events in the activation process of BAX are its translocation to mitochondria and its N-terminal conformational change closely coupled to mitochondrial membrane insertion and oligomerisation. The insertion of BAX into the mitochondrial outer membrane is closely associated with the release into the cytosol of several proteins such as cytochrome c and procaspase-3 which are essential to the execution of the apoptotic program. BAX activation was investigated by Western blot using an antibody that specifically recognizes the activated conformation of BAX. Oly 125 μg/ml treatment of HCT116 cells induced an increase in activated-BAX as compared to non-treated conditions (FIG. 23B). Quantification of the number of BAX positive apoptotic cells revealed that oly significantly affects overall apoptosis as compared with control untreated cells (FIG. 23C).

Recombinant Ostreolysin Interacts with the Cell Membrane and Enters the Cytosol in HCT116 Cells.

As previously reported, selective binding and clustering of oly on chondrocyte membranes, combined with results obtained from artificial membranes and Chinese hamster ovary cells, indicate that the distribution of oly molecules bound to the membranes was not uniformly distributed over the cell surface, but was concentrated in many focal clusters. This suggests that oly recognizes distinct membrane domains that probably serve as attachment sites for aegerolysin-like proteins leading to their aggregation and formation of the pore.

Figure 24:
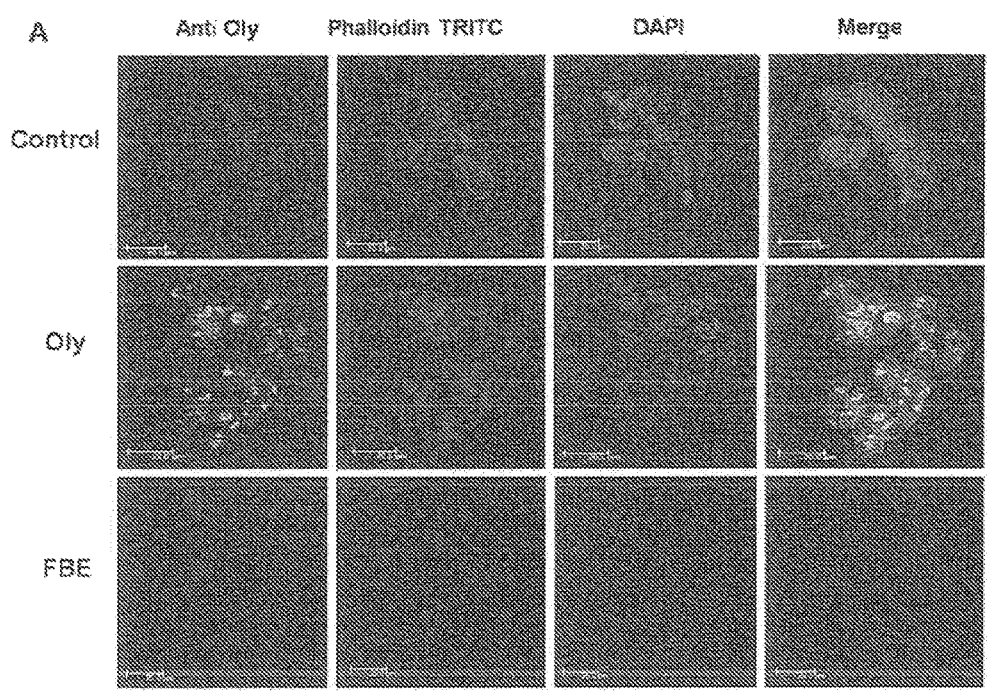
FIG. 24 demonstrates that Ostreolysin penetrates the cell membrane and enters the cytosol. Representative immunofluorescence of HCT116 cells treated for 8 hr, in non treated conditions (control), cells treated with Oly at a concentration of 125 μg/ml, cells treated with FBE at a concentration of 0.01% (w/v) showing the presence of Ostreolysin inside the cells, recognized by the anti-Oly antibody. Scale bar 20 μm.

Next, the membrane distribution of recombinant oly after oly and FBE treatments of HCT116 cells as compared with control conditions, (FIG. 24) were investigated. Cells treated for 8 hours with recombinant oly 125 μg/ml presented a greater distribution of oly-rich domains as compared to control and FBE conditions (FIG. 24). In addition, cross section images of oly treated cells demonstrated that the recombinant oly penetrates the cell membrane and enters the cytosol.

Recombinant Oly Induces Reorganization and Clustering of Cav-1-Rich Membrane in HCT116 Cells.

Figure 25:
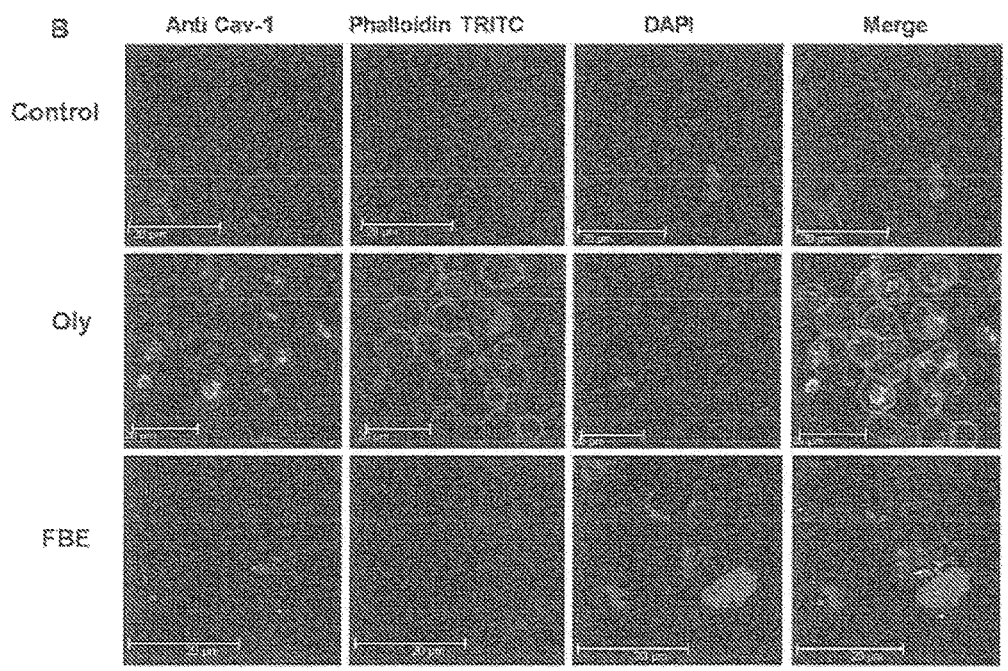
FIG. 25 demonstrates that Ostreolysin induce Caveolin-1 reorganization in lipid rafts. Representative immunofluorescence of HCT116 cells treated for 8 hr in non treated conditions (control), cells treated with Oly at a concentration of 125 μg/ml, cells treated with FBE at a concentration of 0.01% (w/v) showing the clustering of Cav-1 on the membrane, recognized by the anti-Cav-1 antibody. Scale bar 20 μm. As can be seen recombinant Oly enhances the expression of the lipid raft marker Flot-1 in HCT116 cells.
Figure 26:
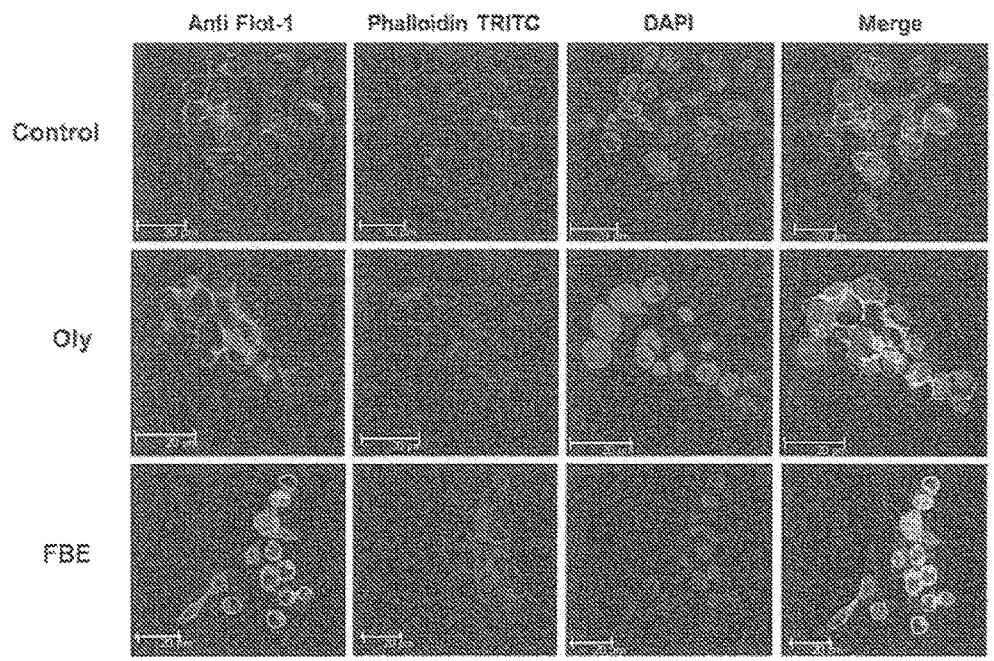
FIG. 26 demonstrates that Ostreolysin does not enhances Flotillin-1 expression in lipid rafts. Therefore, Oly is specific for the raft protein Cav-1. Representative immunofluorescence of HCT116 cells treated for 4 hr in non treated conditions, cells treated with Oly at a concentration of 125 μg/ml and cells treated with FBE at a concentration of 0.01% (w/v) showing the increased expression of Flot-1 on the membrane, recognized by the anti-Flot-1 antibody. Scale bar 20 μm.

It is thought that upon extracellular stimulus, the plasma membrane is prepared for the formation of more stabilized domains and molecular clusters with enhanced size and lifetime such as Caveolae. In order to understand the involvement of Caveolin-1 in apoptosis of colon cancer cells, the effect of oly stimulation on HCT116 cell line was explored (FIG. 25). Caveolae are evident as circular profiles with uniform shape and 50-100 nm in diameter, which are formed by the polymerisation of caveolins leading to the clustering and invagination of existing cholesterol sphingolipid rich domains (lipid rafts) in the cell plasma membrane. Therefore, the membrane distribution of Cav-1 in control conditions and after oly treatment was investigated. Cells treated for 8 hours with oly 125 µg/ml presented a greater number of Cav-1-rich domains as compared to control conditions (FIG. 25). In contrast (FIG. 26) Oly did not induced any notable up-regulation of expression of the lipid-raft associated protein Flotilin-1.

In-Vivo Anticancer Experiments

Figure 27:
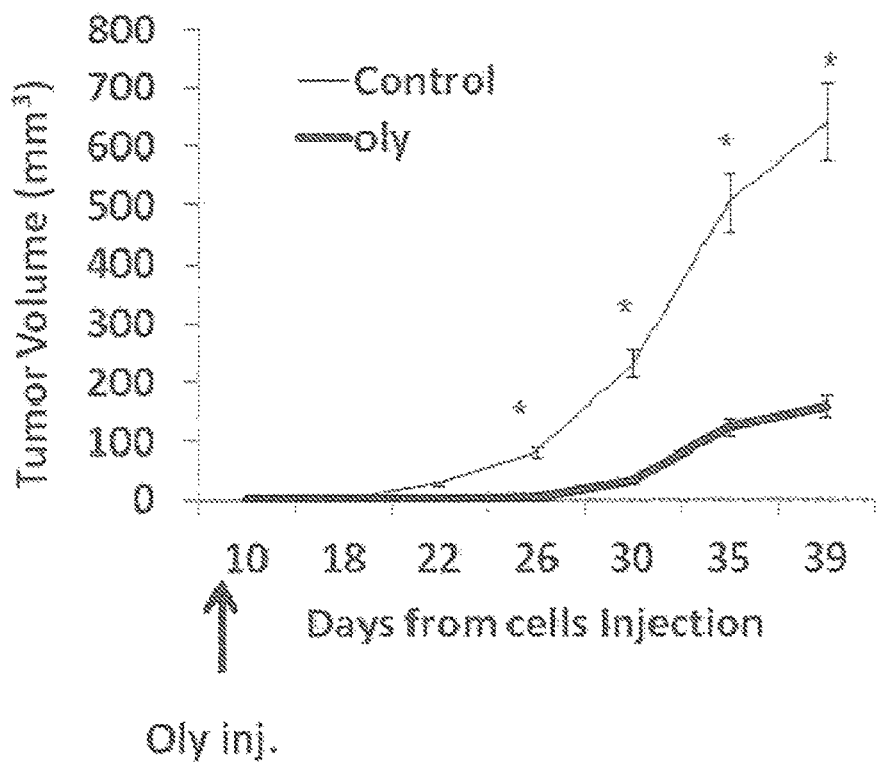
FIG. 27 depicts the effect of Oly on MC38-derived colon cancer cells implanted in C57Bl mice. The cells were injected subcutaneously ($2\times10^5$ cells per mouse) into the left hip. After 10 days of injection and following appearance of tumor signs in some mice, the mice were treated with 1 mg/kg Oly, (3 times a week intraperitoneally). Control mice received PBS three times a week intraperitoneally. Each bar represents the standard error of the mean. N=8 mice; mice were sacrificed on day 39. *=P<0.001.
Figure 28:
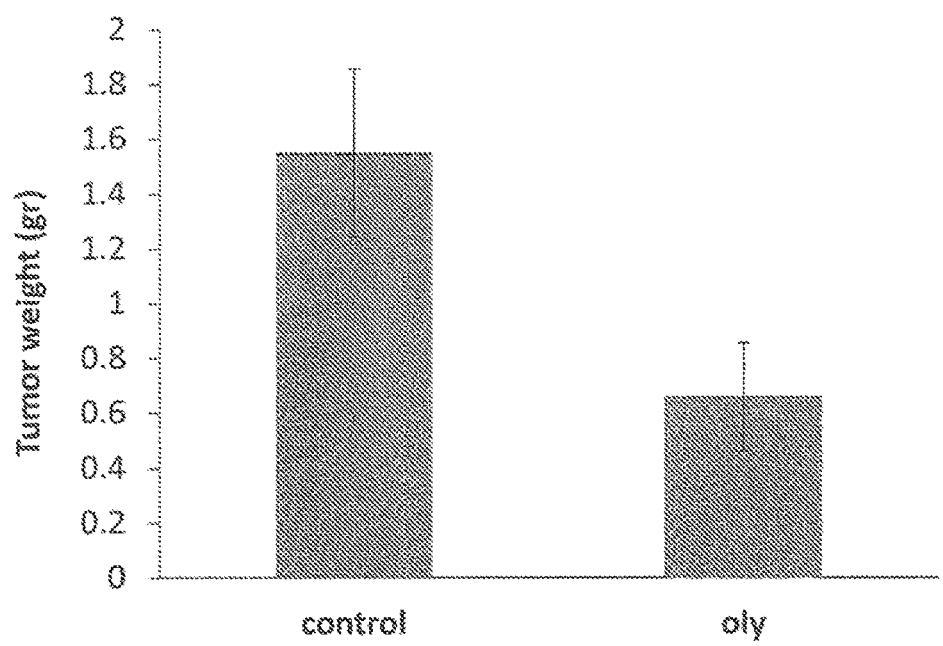
FIG. 28 depicts the effect of Oly on MC38-derived colon cancer cells implanted in C57Bl mice. Tumors were excised after sacrifice and weighed. N=8; *=P<0.001.

C57Bl mice were subcutaneously inoculated with an MC38 colon carcinoma cell line, resulting in development of in situ of very aggressive tumors within 3 weeks after cell inoculation. FIG. 27 demonstrates the effect of Oly on MC38-derived colon cancer cells implanted in C57Bl mice. The cells were injected subcutaneously ($2\times10^5$ cells per mouse) into the left hip. After 10 days of injection and following appearance of tumor signs in some mice, the mice were treated with 1 mg/kg Oly, (3 times a week intraperitoneally). Control mice received PBS 3 times a week intraperitoneally. Each bar represents the standard error of the mean. N=8 mice; mice were sacrificed on day 39. *=P<0.001. As can be seen oly significantly reduced the size of the tumor. FIG. 28 demonstrates the beneficial effect of oly on the tumor weight (which is about half the size of the control).

Example 7

Preparation of Pleurotus ostreatus extracts

Pleurotus ostreatus Preparation Method 1:

Dried powder was prepared from fresh fruiting bodies of Pleurotus ostreatus (Yarden) mushrooms following freezing of fresh fruiting bodies with liquid nitrogen, lyophilizing and afterwards grinding for 1 min. Each 10 gram of powdered fruiting bodies were extracted with 100 ml of cold water (4° C.) by stirring overnight and the mixture was centrifuged at 10,000 rpm for 30 min. The supernatant was filtered, aliquots tested for Oly expression by Western Blot (in the future ELISA methodology to test Oly concentration will be developed) and 10 microliter aliquots were used in order to test the activity in mouse HIB-1B cells.

Pleurotus ostreatus Preparation Method 2:

Dried powder was prepared from fresh fruiting bodies of Pleurotus ostreatus (Yarden) mushrooms by freezing the samples at −20° C., lyophilized and grinding in Moulinex for 1 min. Each 10 gram of powdered fruiting bodies was extracted with 100 ml of cold (4° C.) water by stirring overnight and centrifuged at 10,000 rpm for 30 min. The supernatant was filtered, aliquots tested for Oly expression by Western Blot and 10 microliter aliquots were used in order to test the activity in mouse HIB-1B cells.

Comparison of Oly Concentration in the Two Pleurotus ostreatus Preparations

Figure 29:
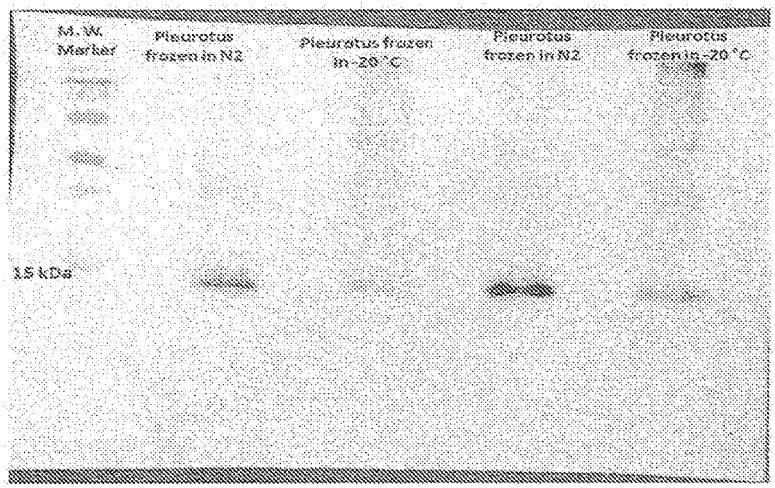
FIG. 29 is a Western blot image showing the concentration of oly in extract preparations of *Pleurotus ostreatus* after freezing in liquid nitrogen (Method 1, lanes 1 and 3) and powdered *Pleurotus ostreatus* after freezing in −20° C. (Method 2, lanes 2 and 4).

As can be seen from FIG. 29 which show the Western blot analysis Oly concentration in extracts from powdered Pleurotus ostreatus after freezing in liquid nitrogen (method 1) are higher than in extracts from powdered Pleurotus ostreatus after freezing at −20° C. (method 2).

Biological Test of the Two Pleurotus ostreatus Preparations

The samples were tested biologically.

The biological test used was the appearance of round bodies resembling intracellular lipid droplets inside HIB-1B cells, which are derived from a brown fat tumor of a transgenic mouse, and are the first established brown adipocyte cell line capable of expressing the brown fat-specific mitochondrial uncoupling protein (UCP).

HIB-1B cells were exposed to 10 µl of a dilution of 1/10 preparation (dilution in distilled sterile water) of Pleurotus ostreatus preparation Method 1 or a similar amount of Pleurotus ostreatus preparation Method 2.

Results (It is noted that for 24 h incubation, similar results were obtained for 48 h incubation; however, the data is not shown)

Figure 30:
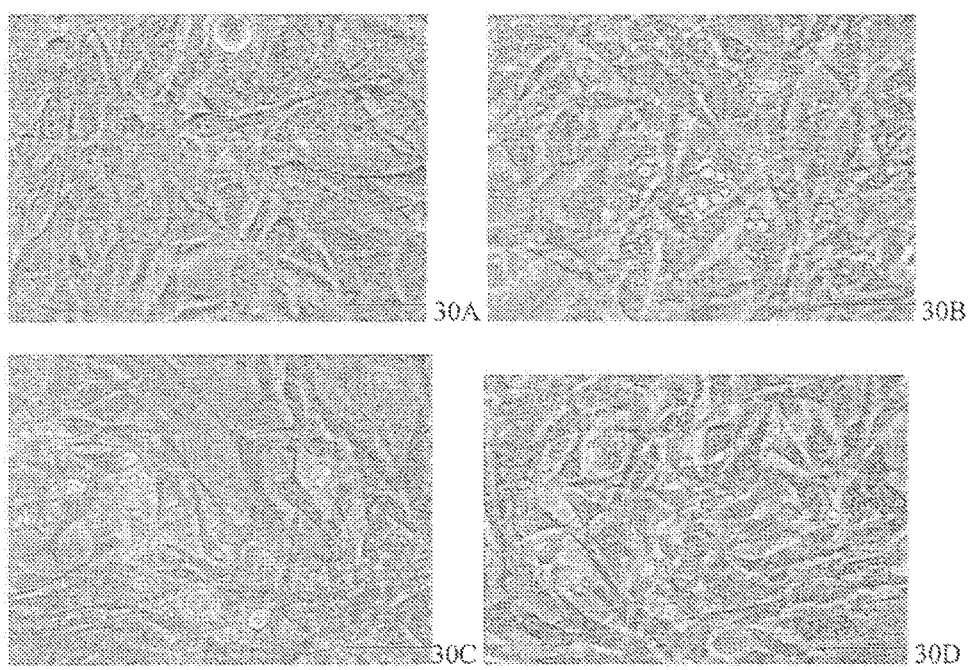
FIGS. 30A-D show control (30A), oly 10 µg/ml (30B), and extract preparations of *Pleurotus ostreatus* after freezing in liquid nitrogen (30C), and powdered *Pleurotus ostreatus* after freezing in −20° C. (30D).

As can be seen from FIG. 30, in the control HIB-1B cells no lipid droplets were seen (FIG. 31A). In the Oly (10 µg/ml) treated HIB-1B cells many lipid droplets can be seen (FIG. 31B). In the Pleurotus ostreatus preparation Method 1-treated HIB-1B cells.

HIB-1B cells treated with fruiting bodies extract from Pleurotus ostreatus according to Method 1. Lipid droplets were seen in an amount which was similar to that of the oly treated cells (FIG. 31C). Similarly, as can be seen from FIG. 31D, which show the Pleurotus ostreatus preparation Method 2-treated HIB-1B cells, the amount of lipid droplets in the cells was similar to the amount of the droplets in the oly treatment.

In conclusion both methods of preparation of the extracts resulted in a sufficient Oly-like activity. Even at lower concentrations of oly, the preparations are effective. Therefore, it is expected that in-vivo administration of these Pleurotus ostreatus mushroom isolates will induce as anti-obesity, anti-insulin resistance, anti-cancer and anti-fatty liver effects as was shown for the recombinant oly.

It will be appreciated by persons skilled in the art that the present invention is not limited by what has been particularly shown and described herein above. Rather the scope of the invention is defined by the claims that follow.

The invention claimed is:

1. A method of enhancing production of brown fat adipocytes, or promoting brown adipocyte differentiation, the method comprising contacting a precursor of brown fat adipocytes with an effective amount of *Pleurotus* mushroom extract comprising oly or a composition comprising *Pleurotus* mushroom extract comprising OLY, so as to enhance production of brown fat adipocytes or promote brown adipocyte differentiation.

2. The method of claim 1, wherein the enhancing of production of brown fat adipocytes or promoting brown adipocyte differentiation is effective in treating overweight or obesity in a subject in need thereof.

3. The method of claim 1, wherein the extract or the composition is in a form of a powder, solution, suspension, emulsion, tablet, enteric coated tablet, or capsule, gel, cream, ointment, foam, paste or injection.

4. The method claim 1, wherein the *Pleurotus* mushroom is a *Pleurotus ostreatus* mushroom or a *Pleurotus pulmonarious* mushroom.

5. The method of claim 1, wherein the precursor of brown fat adipocytes is a stem cell, mesenchymal stem cell, myogenic precursor, brown pre-adipocyte and white pre-adipocyte.

6. The method of claim 1, wherein the extract or the composition are in a formulation, which is a nutraceutical composition or a dietary supplement, wherein the formulation comprises a carrier suitable for food consumption.

7. A method of differentiating white adipocyte into brown adipocyte in a cell or inducing brown adipogenesis comprising contacting the cell with an effective amount of *Pleurotus* mushroom extract comprising oly or a composition comprising *Pleurotus* mushroom extract comprising OLY.

8. The method of claim 7, wherein the differentiating of white adipocyte into brown adipocyte in a cell or inducing brown adipogenesis is effective in treating overweight or obesity in a subject in need thereof.

9. The method of claim 7, wherein the extract or the composition is in a form of a powder, solution, suspension, emulsion, tablet, enteric coated tablet, or capsule, gel, cream, ointment, foam, paste or injection.

10. The method claim 7, wherein the *Pleurotus* mushroom is a *Pleurotus ostreatus* mushroom or a *Pleurotus pulmonarious* mushroom.

11. The method of claim 7, wherein the extract or the composition are in a formulation, which is a nutraceutical composition or a dietary supplement, wherein the formulation comprises a carrier suitable for food consumption.

* * * * *